United States Patent [19]
Benet et al.

[11] Patent Number: 5,665,386
[45] Date of Patent: Sep. 9, 1997

[54] USE OF ESSENTIAL OILS TO INCREASE BIOAVAILABILITY OF ORAL PHARMACEUTICAL COMPOUNDS

[75] Inventors: Leslie Z. Benet, Belvedere; Vincent J. Wacher, San Francisco; Reed M. Benet, Belvedere, all of Calif.

[73] Assignee: AvMax, Inc., Berkeley, Calif.

[21] Appl. No.: 486,186

[22] Filed: Jun. 7, 1995

[51] Int. Cl.$^6$ ................................... A61K 9/48
[52] U.S. Cl. .................. 424/451; 424/455; 424/456; 514/946
[58] Field of Search ................. 424/456, 465, 424/449, 451, 455; 514/946

[56] References Cited

U.S. PATENT DOCUMENTS

| | | | |
|---|---|---|---|
| 4,822,816 | 4/1989 | Markham | 514/474 |
| 4,849,227 | 7/1989 | Cho | 424/498 |
| 4,944,949 | 7/1990 | Story et al. | 424/481 |
| 4,968,716 | 11/1990 | Markham | 514/474 |
| 5,070,085 | 12/1991 | Markham | 514/161 |
| 5,156,842 | 10/1992 | Mulligan | 424/451 |
| 5,179,122 | 1/1993 | Greene et al. | 514/458 |
| 5,284,657 | 2/1994 | Lu et al. | 424/435 |
| 5,332,747 | 7/1994 | Van Dyke | 514/280 |
| 5,350,756 | 9/1994 | Smith | 514/289 |
| 5,409,690 | 4/1995 | Howell et al. | 424/10 |
| 5,422,350 | 6/1995 | Woolf | 514/252 |
| 5,424,289 | 6/1995 | Yang et al. | 514/12 |
| 5,436,243 | 7/1995 | Sachs et al. | 514/252 |
| 5,455,286 | 10/1995 | Amidon et al. | 523/122 |
| 5,466,696 | 11/1995 | Woolf | 514/297 |

FOREIGN PATENT DOCUMENTS

| | | |
|---|---|---|
| 0 127 677 | 8/1990 | European Pat. Off. . |
| 2 706 771 | 12/1994 | France . |
| WO90/12583 | 11/1990 | WIPO . |
| WO92/06680 | 4/1992 | WIPO . |

OTHER PUBLICATIONS

Bonkvosky et al., *Cytochrome $P_{450}$ of Small Intestinal Epithelial Cells*, Gastroenterology, 88:458–467 (1985).

Bradford, *A Rapid and Sensitive Method for the Quantification of Microgram Quantities of Protein Utilizing the Principle of Protein–Dye Binding*, Analytical Biochemistry, 72:248–254 (1976).

Hait et al., *Terfenadine (Seldane®): A New Drug for Restoring Sensitivity to Multidrug Resistant Cancer Cells*, Bioch. Pharm., 45(2):401–406 (1993).

Hsing et al., *The Function of Gp170, the Multidrug–Resistance Gene Product, in the Brush Border of Rat Intestinal Mucosa*, Gastroenterology, 102:879–885 (1992).

Kronbach et al., *Cyclosporine Metabolism in Human Liver: Identification of a Cytochrome P–450III Gene Family as the Major Cyclosporine–Metabolizing Enzume Explains Interactions of Cyslosporine with Other Drugs*, Clin. Pharmacol. Ther., 43(6)630–635 (1988).

Nash, *The Colorimetric Estimation of Formaldehyde by Means of the Hantzsch Reaction*, Biochem., 55:416–421 (1953).

Nielsen et al., *P–Glycoprotein as Multidrug Transporter: A Critical Review of Current Multidrug Resistant Cell Lines*, Chimica et Biophysica Acta., 1139:169–183 (1992).

Omura et al., *The Carbon Monoxide–Binding Pigment of Liver Microsomes*, J. Biol. Chem., 239(7):2370–2378 (1964).

Schmiedlin et al., *Cultured Adult Rat Jejunal Explants as a Model for Studying Regulation of CYP3A*, Biochemical Pharmacology, 46(5):905–918 (1993).

Watkins et al., *Identification of Glucocorticoid–Inducible Cytochromes P–450 in the Intestinal Mucosa of Rats and Man*, J. Clin. Invest., 80:1029–1036 (1987).

Wrighton et al., *Demonstration in Multiple Species of Inducible Hepatic Cytochromes P–450 and Their mRNAs Related to the Glucorcorticoid–Inducible Cytochrome P–450 of the Rat*, Molecular Pharmacology, 28:312–321 (1985).

Yoda et al., *On the Reversibility of Binding of Cardiotonic Steroids to a Partially Purified (Na+K)–Activated Adenosinetriphosphatase from Beef Brain*, Biochemical and Phisical Reserch Communications, 40(4):880–887 (1970).

Adams, M.W., *d–Alpha Tocopheryl Polyethylene glycol 1000 Succinate (Eastman vitamin E TPGS) as an Emulsifier and Bioenhancer for Drugs and Lipophilic Compounds*, 6th International Conference on Pharmaceutical technology, Paris, 2–4 Jun., 1992.

Albengres et al., "Cyclosporin and Ketoconazole, Drug Interaction or Therapeutic Association?", International Journal of Clinical Pharmacology et al., 30(12): 555–570, 1992.

Arias, I.M. et al., "Structure & Function of P–Glycoprotein in the Normal Liver", Xenobiotics and Cancer (L. Ernster et al., eds.), Japan Sci. Soc. Press, Tokyo/Taylor & Francis, Ltd., London, pp. 229–239, 1991.

(List continued on next page.)

*Primary Examiner*—Thurman K. Page
*Assistant Examiner*—James M. Spear
*Attorney, Agent, or Firm*—Cooley Godward LLP

[57] ABSTRACT

A method for increasing bioavailability and reducing inter- and intra-individual variability of an orally administered hydrophobic pharmaceutical compound, which comprises orally administering the pharmaceutical compound to a mammal in need of treatment with the compound concurrently with an essential oil or essential oil component in an amount sufficient to provide bioavailability of the compound in the presence of the essential oil or essential oil component greater than bioavailability of the compound in the absence of the essential oil or essential oil component, wherein the essential oil or essential oil component has an activity of at least 10% inhibition at a concentration of 0.01 wt. % or less in an assay that measures conversion of cyclosporine to hydroxylated products using an assay system containing 250 µg rat liver microsomes, 1 µM cyclosporine, and 1 mM reduced nicotinamide adenine dinucleotide phosphate (NADPH) in 1 ml of 0.1M sodium phosphate buffer, pH 7.4.

10 Claims, No Drawings

OTHER PUBLICATIONS

Akitoshi et al., Abstract "Acceleration of Transdermal Absorption of Pharmaceuticals by Essential Oils and Organic Solvents", Chem Abst., 112:125228t, 1990.

Baciewicz et al., "Ketoconazole and Fluconazole Drug Interactions", Archives of Internal Medicine, 153(17):1970–76, 1993.

Back et al., "Comparative Effects of two Antimycotic Agents, Ketoconazole and Terbinafine on the Metabolism of Tolbutamide, Ethinyloestradiol, Cyclosporin and Ethoxycoumarin by Human Liver Microsomes In Vitro", British Journal of Clinical Pharmacology, 28:166–170, 1989.

Back et al., "Azoles, Allylamines and Drug Metabolism", British Journal of Dermatology, Supplement 39, 126:14–18, 1992.

Back, David J., and Orme, Michael L'E.; "Pharmacokinetic Drug Interactions with Oral Contraceptives", (1990) Clin. Pharmacokinet. 18(6):472–484.

Callaghan, Richard and Riordan, John R.; "Synthetic and Natural Opiates Interact with P–glycoprotein in Multidrug–resistant Cells", (1993) J. Biol. Chem. 268 (21):16059–16064.

Chan et al., "Drug Interactions with Cyclosporine: Focus on Antimicrobial Agents", Clinical Transplantation, 6: (3) (1):141–153, Jun. 1992.

Chang, Tammy et al., "The Effect of Water–Soluble Vitamin E on Cyclosporine Pharmacokinetics in healthy Volunteers", Abstract in American Society to Clinical Pharmacology and Therapeutics, 57 (2):163, Feb 1995.

Clynes, Martin; "Cellular Models for Multiple Drug Resistance in Cancer", (1993) In Vitro Cell. Dev. Biol. 29A:171–179.

de Smet et al., "Combined use of Cyclosporine and Ketoconazole in the treatment of Endogenous Uveitis", American Journal of Ophthalmology, 113:687–690, Jun. 1992.

Endicott, Jane A., and Ling, Victor; "The Biochemistry of P–glycoprotein–mediated Multidrug Resistance", (1989) Annu. Rev. Biochem. 58:137–171.

Fahr, Alfred; "Cyclosporin Clinical Pharmacokinetics", (1993) Clin. Pharmacokinetic 24 (6):472–495.

Fairchild, Craig R., and Cowan, Kenneth H.; "Keynote Address: Multidrug Resistance: A Pleiotropic Response To Cytotoxic Drugs" (1991) Int. J. Radiation Oncology Biol. Phys. 20:361–367.

Fasco, Michael J. et al.; "Rat Small Intestinal Cytochromes P450 Probed by Warfarin Metabolism" (1993) Mol. Pharmacol. 43:226–233.

First et al., "Concomitant Administration of Cyclosporin and Ketoconazole in Renal Transplant Recipients", The Lancet, 2:1198–1201, Nov. 18, 1989.

First et al., "Cyclosporine Dose Reduction by Ketoconazole Administration in Renal Transplant Recipients", Transplantation, 51 (2): 365 –370, Feb. 1991.

Fojo, Antonio T.; "Multidrug Resistance" (1991) Adv. Intern. Med. 36:195–218.

Gatmaitan, Zenaida C. and Irwin M. Arias; "Structure and Function of P–Glycoprotein in Normal Liver and Small Intestine" (1993) Adv. Pharmacol. 24: 77–97.

Greenblatt. David J.; "Presystemic Extraction: Mechanisms and Consequences"(1993) J. Clin. Pharmacol 33: 650–656.

Hebert, Mary F. et al.; "Bioavailability of Cyclosporine with Concomitant Rifampin Administration is Markedly Less Than Predicted by Hepatic Enzyme Induction" (1992) Clin. Pharmacol. Ther. 52:453–457.

Henricsson et al., "Cyclosporin Metabolism in Human Liver Microsomes and its Inhibition by Other Drugs", Pharmacology & Toxicology, 66:49–52, 1990.

Hunter, J. et al., "Epithelial Secretion of Vinblastine by Human Intestinal Adenocarcinoma Cell (HCT–8 and T84) Layers Expressing P–Glycoprotein", British Journal of Cancer, 64:437–444, 1991.

Hunter, Janice et al.; "Functional Expression of P–glycoprotein in Apical Membranes of Human Intestinal Caco–2 Cells", (1993) J. Biol Chem. 268:14991–14997.

Jancis, Erik M. et al.; "Estradiol Induction of Rhodamine 123 Efflux and the Multidrug Resistance Pump in Rat Pituitary Tumor Cells" (1993) Mol. Pharmacol. 43:51–56.

Kaminsky, Laurence, and Michael J Fasco; "Small Intestinal Cytochromes P450". (1992) Toxicology 21 (6):407–422.

Kolars, Joseph C. et al.; "Identification of Rifampin–inducible P450IIIA4 (CYP3A4) in Human Small Bowel Enterocytes" (1992) J. Clin. Invest. 90:1871–1878.

Kolars, Joseph C. et al.; "Heterogeneity of Cytochrome P450IIIA Expression in Rat Gut Epithelia" (1992) Gastroenterology 102:1186–1198.

Kolars, Joseph C. et al.; "Cyclosporine Metabolism by P450IIIA in Rat Enterocytes—Another Determinant of Oral Bioavailability?" (1992) Transplantation 53:596–602.

Komori, Masayuki et al.; "Cytochrome P–450 in Human Liver Microsomes: High–Performance Liquid Chromatographic Isolation of Three Forms and Their Characterization" (1988) J. Biochem. 104:912–916.

Kralovanszky, et al.; "Isolation of Viable Intestinal Epithelial Cells and Their Use for in Vitro Toxicity Studies", In Vivo 4:201–204, 1990.

Kronbach, Thomas et al.; "Oxidation of Midazolam and Triazolam by Human Liver Cytochrome P450IIIA4" (1989) Molec. Pharm. 36:89–96.

Lalka et al.; "The Hepatic First–Pass Metabolism of Problematic Drugs" (1993) J. Clin. Pharmacol. 33:657–669.

Ludescher et al.; "Rapid Functional Assay for the Detection of Multidrug–Resistant Cells Using the Fluorescent Dye Rhodamine 123 (Letter; Comment)" (1991) Blood 78 (5):1385–1387.

Ludescher et al.; "Detection of Activity of P–Glycoprotein in Human Tumor Samples Using Rhodamine 123" (1992) Br. J. Haematol 82:161–168.

Lum et al.; "Clinical Trials of Modulation of Multidrug Resistance. Pharmacokinetic and Pharmacodynamic Considerations" (1993) Cancer 72:3502–3514.

Lum et al.; "Molecular Targets in Oncology: Implications of the Multidrug Resistance Gene" (1993) Pharmacotherapy, 13:88–109.

Muranishi, Shozo; "Absorption Enhancers" (1990) Crit. Rev. Ther. Drug Carrier Sys., 7:1–33.

Pearce et al., "Essential Features of the P–Glycoprotein Pharmacophore as Defined by a Series of Reserpine Analogs That Modulate Multidrug Resistance" (1989) Proc. Natl. Acad. Sci., 86:5128–5132.

Peters, W.H. et al., "Expression of Drug–Metabolizing Enzymes and p–170 Glycoprotein in Colorectal Carcinoma and Normal Mucosa", Gastroenterology 103:448–455, 1992.

Pichard et al., "Cyclosporine A Drug Interactions: Screening for Inducers and Inhibitors of Cytochrome P–450 (Cyclosporine A Oxidase) in Primary Cultures of Human Hepatocytes and in Liver Microsomes" (1990) Drug Metab. Dipos. 18:595–606.

Pichard, L., et al., "Effect of Corticosteroids on the Expression of Cytochromes P450 and on Cyclosporin A Oxidase Activity in primary Cultures of Human Hepatocytes", Molecular Pharmacology, 41(6): 1047–1055, 1992.

Sands, M., et al., "Interactions of Cyclosporine with Antimicrobial Agents", Reviews of Infectious Diseases, 11:(5)691–697, Sep.–Oct. 1989.

Somberg et al.; "The Clinical Implications of First–Pass Metabolism: Treatment Strategies for the 1990's" (1993) J. clin. Pharmacol. 33:670–673.

Sridhar, T. J., et al., "Influence of Concomitant Medication on Cyclosporine Dosage and Blood Concentrations in Renal Allograft Recipients", Clinical Transplantation, 6(2)134–138, Apr. 1992.

Tam, Yun K.; "Individual Variation in First–Pass Metabolism" (1993) Clin. Pharmacokinet. 25:300–328.

Thierry et al.; "Modulation of Doxorubicin Resistance in Multidrug–Resistant Cell by Liposomes" (1993) FASEB J. 6:572–579.

van Hoogdalem et al.; "Intestinal Drug Absorbtion Enhancement: An Overview" (1989) Pharmacol. Ther. 44:407–443.

Warren et al.; "Increased Accumulation of Drugs in Multidrug–Resistant Cell Induced by Liposomes" (1992) Cancer Research 52:3241–3245.

Watkins, Paul B.; "The Role of Cytochromes P–450 in Cyclosporine Metabolism" (1990) J. Am. Acad. Dermacol. 23:1301–1309.

Watkins et al.; "Erythromycin Breath Test as an Assay of Glucocorticoid–Inducible Liver Cytochromes P–450" (1989) J. Clin. Invest. 83:688–697.

Watkins, Paul B., "Drug Metabolism by Cytochromes P450 in the Liver and Small Bowel" (1992) *Gastrointestinal Pharmacology* 21 (3) :511–527.

West, I.C.; "What Determines the Substrate Specificity of the Multi–Drug Resistance Pump?" (1990) TIBS 15:42–46.

Wrighton et al.; "Studies on the Expression of Metabolic Capabilities of Human Liver Cytochrome P450IIIA5 (HLp3)" (1990) Molec. Pharmacol. 37:207–213.

Wrighton et al.; "In Vitro Methods for Assessing Human Hepatic Drug Metabolism: Their use in Drug Development" (1993) 25:453–484.

Wu et al.; "Use of IV and Oral Drug Levels from Cyclosporene (CsA) with Concomitant Rifampin to Differentiate Gut Absorbtion and Metabolism" (1993) Pharm. Res. 10:abstract ppdm8185.

Yee et al., "Pharmacokinetic Drug Interactions with Cyclosporin (Part I)", Clinical Pharmacokinetics, 19(4):319–332, 1990.

Zamora et al.; "Physical–Chemical Properties Shared by Compounds that Modulate Multidrug Resistance in Human Leukemic Cells" (1988) Molec. Pharmacol. 33:454–462.

USE OF ESSENTIAL OILS TO INCREASE BIOAVAILABILITY OF ORAL PHARMACEUTICAL COMPOUNDS

INTRODUCTION

1. Technical Field

This invention is directed to the field of pharmacology and particularly to the formulation of oral pharmaceutical compositions for increased bioavailability and reduced inter- and intra-individual variability.

2. Background

Pharmacokinetics is the study of the fate of pharmaceuticals from the time they are ingested until they are eliminated from the body. The sequence of events for an oral composition includes absorption through the various mucosal surfaces, distribution via the blood stream to various tissues, biotransformation in the liver and other tissues, action at the target site, and elimination of drug or metabolites in urine or bile.

Bioavailability of a drug (pharmaceutical composition) following oral dosing is a critical pharmacokinetic determinant which can be approximated by the following formula:

$$F_{oral} = F_{ABS} \times F_G \times F_H$$

$F_{oral}$ is oral bioavailability fraction, which is the fraction of the oral dose that reaches the circulation in an active, unchanged form. $F_{oral}$ is less than 100% of the active ingredient in the oral dose for four reasons: (1) drug is not absorbed out of the gut lumen into the cells of the intestine and is eliminated in the feces; (2) drug is absorbed into the cells of the intestine but back-transported into the gut lumen; (3) drug is biotransformed by the cells of the intestine (to an inactive metabolite); or (4) drug is eliminated by the cells of the liver, either by biotransformation and/or by transport into the bile. Thus, oral bioavailability is the product of the fraction of the oral dose that is absorbed ($F_{ABS}$), the fraction of the absorbed dose that successfully reaches the blood side of the gastrointestinal tract ($F_G$), and the fraction of the drug in the GI blood supply that reaches the heart side of the liver ($F_H$). The extent of gut wall absorption, back transport and metabolism, and liver elimination are all subject to wide inter- and intra-individual variability.

Previous investigations arising in the laboratory of one of the present inventors resulted in new understandings of factors involved with bioavailability and in the invention described in U.S. patent application Ser. No. 08/190,288, film 2 Feb. 1994 U.S. Pat. No. 5,567,592. This application described general methods for increasing bioavailability of oral pharmaceutical compositions and methods for identifying compounds that had increased bioavailability. However, although that invention made it possible to investigate a number of classes of compounds not previously thought to be useful in enhancing bioavailability, the actual process of identifying specific classes of compounds that are superior bioenhancers, among those bioenhancers which work to some degree, still remains a process of investigation and discovery. Within many classes of substances identified as showing general bioenhancing effects, there is surprising variance from class member to class member in the extent of each compound's bioenhancing effect, and some compounds that would at first thought appear to be enhancers of drug bioavailability because of their membership in a generally effective class of compounds, actually are found to be agents that interfere with the bioavailability of drugs, although the mechanism by which such interference takes place is not yet known. In some cases, a single compound or small group of compounds has been found to be particularly potent as a bioenhancer despite resembling in structure other compounds that have less activity or that even reduce bioavailability.

Accordingly, it is important to identify and confirm the identity of classes of compounds or individual compounds that are particularly useful for enhancing bioavailability.

SUMMARY OF THE INVENTION

An object of this invention is to identify compositions with superior ability to increase drug bioavailability, particularly by decreasing drug biotransformation in the gut wall by inhibiting cytochrome P450 drug metabolism and/or increasing net drug absorption through the gut wall by inhibiting P-glycoprotein (P-gp) drug transport.

Another object of the invention is to provide compositions that strongly inhibit enzymes of the cytochrome P450 3A class (CYP3A) in the gut in preference to in other locations, such as the liver, which was previously thought to be the primary site of drug metabolism.

A further object of the invention is to provide compositions that strongly inhibit P-gp-controlled back transport to increase the net transport of drugs through the enterocyte layer and cause an increase in the bioavailability of a coadministered drug, since the protein P-gp pumps drugs that have been transported into the cytoplasm of enterocytes back into the lumen of the gut.

One specific object of the present invention is to reduce inter-individual variability of the systemic concentrations of the active pharmaceutical compound, as well as intra-individual variability of the systemic concentrations of the pharmaceutical compound being administered.

The invention is carried out by co-administering one or more essential oils with an oral pharmaceutical compound (drug) or compounds to increase drug bioavailability. The compositions and methods of the invention can be used to increase drug efficacy in humans and in other mammals. Although veterinary use is specifically contemplated, the primary use will be in human treatment. Administration schemes include, but are not limited to, use of oral and topical formulations in humans and use of similar formulations for livestock.

DESCRIPTION OF SPECIFIC EMBODIMENTS

Essential Oils Increase Drug Bioavailability

The present invention arises from continued research into the factors affecting drug bioavailability that were described in an earlier application arising from the laboratory of one of the present inventors. "Drug bioavailability" is defined here as the total amount of drug systemically available over time. The present invention increases drug bioavailability by inhibiting drug biotransformation in the gut and/or by inhibiting active back transport systems in the gut that decrease the net transport of drugs across gut epithelia into the bloodstream. In either case the composition responsible for increased drug bioavailability is an essential oil. For reasons that are not immediately apparent, it has been discovered that essential oils, as a class, are typically capable of inhibiting the appropriate enzyme and/or transport system, despite the chemical differences that exist among the individual compounds that are found in the essential oils.

The inventors theorize that the mechanisms for such inhibitory effect may result directly or indirectly from the course of mammalian evolution. In general, the botanicals in which the essential oils and essential oil components belong have always been the mainstay of the mammalian food supply. To produce an effect, they simply require to be consumed and they are consumed directly without preparation (although not in the concentrated form of an essential oil or isolated essential oil component). In the course of consumption, related biochemical mechanisms may have evolved for the direct advantage of the mammalian organism or as an indirect result of evolutionary accident or imperative. Thus, while the essential oils and essential oil components evidence chemical differences, the similar source of their origin, the similarity of their location in the mammalian food supply, perhaps the similarity of their direct or indirect effect on the evolution of the mammalian organism, and certainly their similarity in effect on the mammalian organism leads to the reasonable conclusion that essential oils can be considered as a cohesive class of compounds of an importance even beyond what ties them together by technical definition, namely that essential oils are predominately volatile materials or materials isolated by some physical (as opposed to chemical) process from an odorous, single-species botanical source.

In general, the present invention provides a method for increasing the bioavailability of an orally administered pharmaceutical compound (particularly one which is hydrophobic) by orally administering the pharmaceutical compound to a mammal in need of treatment concurrently with an essential oil in sufficient amount to provide integrated systemic concentrations over time of the compound greater than the integrated systemic concentrations over time of the compound in the absence of the essential oil. Changes in the integrated systemic concentrations over time are indicated by "area under the curve" (AUC) measurements, an accepted pharmacological technique described in detail below.

Essential Oils

For the purposes of this invention, an essential oil is a predominately volatile material or materials isolated by some physical (as opposed to chemical) process from an odorous, single-species, botanical source. The most widely used process for the isolation of essential oils is steam distillation of plant matter, although dry distillation and solvent extraction are also used. A botanical source is odorous if an odor can be detected by any animal, not just a human; "odorous" thus is simply an indication that some volatile component is present in the plant. The oils extracted by the physical process can contain some non-volatile material, as is well known in the art. Essential oils have been known for centuries in many cases and even millennia, and this term is well known in the art. Essential oils are available commercially (even to the extent of being available in carload lots) because of their common use as flavorings for food. The names used for essential oils in Table 1 below are commonly recognized commercial names.

Since the individual components of the essential oils are the individual compounds that will interact with enzymes and transport proteins in the manner described herein, it is apparent that essential oil components that are sufficiently active will also be useful in the practice of the invention. However, it would be awkward to always refer to "essential oil or essential oil component," so in this application "essential oil" (or "essential oils") refers to both entire essential oils as obtained from plants and to individual components of essential oils, such as those listed in Table 2 below. Where more precision is needed to refer to components of essential oils as distinct from full essential oil mixtures, the components are expressly referred to. When it is appropriate to distinguish essential oils as a class from "essential oils and essential oil components," the phrase "essential oil extract" or "full essential oil" is used if the meaning is not clear from the context.

Because some few essential oils and essential oil components are of low activity and thus not likely to be useful for the purposes described generally herein, only those essential oils and essential oil components that have an activity of at least 10% inhibition at a concentration of 0.01 wt. % or less in an assay that measures conversion of cyclosporine to hydroxylated products using an assay system containing 250 µg rat liver microsomes, 1 µM cyclosporine, and 1 mM reduced nicotinamide adenine dinucleotide phosphate (NADPH) in 1 ml of 0.1M sodium phosphate buffer, pH 7.4, are considered to be within the meaning of "essential oil" and thus within the invention as described herein. Preferred are those full oils and components that show an inhibition of at least 60% at a concentration of 0.01%; more preferred are those full oils and components that show an inhibition of at least 40% at a concentration of 0.001%; even more preferred are those full oils and components that show an inhibition of at least 20% at a concentration of 0.0001%. A detailed description of this assay system is set out in the example below.

A number of essential oils are used for their flavors and odors and are recognized by the Code of Federal Regulations, Title 21, as GRAS (generally recognized as safe) compositions that do not require regulatory agency approval before they are included in ingested materials. See particularly parts 182.10, 182.20, 182.40, 182.50, and 182.60 of 21 CFR. Additional essential oils and components of essential oils are identified in 21 CFR 172.510 and 172.515 as having been used previously in foods, although they are not on the GRAS list. A number of important essential oils are set out in Table 1 below, although the invention is not limited to the specific essential oils (and components) listed individually in the specification. In this and other tables in this specification showing inhibition, inhibition is measured from the solvent baseline (usually ethanol or other solvents as described below). The reason for higher variability of results on repeats for lower concentrations of oils is unknown, but may be due to evaporation of components when only small amounts are present.

TABLE 1

ESSENTIAL OILS

| CAS# | CFR# | Name | Latin name | 0.01% | SD | repeat 0.01 (SD) | 0.001% | SD | repeat 0.001 (SD) | 0.0001% | SD | repeat 0.0001(SD) | 0.00001% | SD |
|---|---|---|---|---|---|---|---|---|---|---|---|---|---|---|
| 8006-77-7 | 182.20 | Allspice Berry Amber Essence | *Pimenta officinalis* L. | 100 54 | 0 1 | | 74 | 2 | | 32 | 2 | | | |
| 84775-42-8 | 182.20 | Anise Seed | *Pimpinella anisum* L. | 91 | 10 | | 29 | 5 | | | | | | |
| 68990-11-4 | 172.510 | Arnica (20%) | *Arnica* spp. | 35 | 3 | | | | | | | | | |
| 8007-00-9 | 182.20 | Balsam of peru | *Myroxylon pereirae* Klotzsch | obscured | | | 6 | 3 | | | | | | |
| 8015-73-4 | 182.20 | Basil | *Ocimum basilicum* L. | 91 | 2 | | 59 | 1 | | | | | | |
| 91721-75-4 | 182.20 | Bay Leaf (Myrcia) | *Pimenta acris* Kostel | 91.3 | 0.5 | | 57.9 | 0.5 | | | | | | |
| 9000-05-9 | 172.510 | Benzoin Gum | *Styrax* spp. | 100 | 0 | | 100 | 0 | | 40 | | | 22 (3); −6 (13) | |
| 8007-75-8 | 182.20 | Bergamot | *Citrus aurantium* L. subsps. *bergamia* Wright et Arn. | 99 | 2 | | 46.4 | 0.2 | | | | | | |
| 8015-77-8 | 182.20 | Bois de Rose (Rosewood) | *Aniba roseaeodora* Ducke | 94.9 | 0.2 | 100 (0) | 53 | 3 | | | | | | |
| 8008-98-8 | 172.510 | Cajeput | *Melaleuca* ssp. | 91.5 | 0.4 | | 56 | 4 | | | | | | |
| | 182.20 | Calendula (Marigold pot) | *Calendula officinalis* L. | 19 | 6 | | | | | | | | | |
| 8008-51-3 | 172.510 | Camphor, White | *Cinnamomum camphora* L. Nees et Eberm. (Safrole free) | 89 | 1 | 87 (3) | 45 | 5 | | | | | | |
| 8000-42-8 | 182.20 | Caraway Seed | *Carum carvi* L. | 92 | 4 | | 59 | 1 | | | | | | |
| 8000-66-6 | 182.20 | Cardamon | *Elleteria cardamomum* (L.) Maton | 99 | 1 | 100 (0) | 64 | 1 | | 7 | 6 | | | |
| 8015-88-1 | 182.20 | Carrot Seed | *Daucus carota* L. | 100 | 0 | | 81.6 | 0.1 | | 52 | 1 | 45 (2); 3 (10) | | |
| 68990-83-0 | 172.510 | Cedarwood | *Thuja occidentalis* L. (Thujone free) | 100 | 0 | | 95 | 4 | | 56 | 2 | 74 (1); 12 (4) | | |
| 8015-90-5 | 182.20 | Celery | *Apium graveolens* L. | 91 | 3 | | 66 | 3 | | | | | | |
| 8002-66-2 | 182.20 | Chamomile, German or Hungarian | *Matricaria chamomilla* L. | 98.4 | 0.2 | | 66 | 2 | | | | | | |
| 8015-92-7 | 182.20 | Chamomile, Roman or English | *Anthemis nobilis* L. | 100 | 0 | | 69 | 2 | | | | | | |
| 8015-91-6 | 182.20 | Cinnamon | *Cinnamomum* spp. | 78 | 2 | | 29 | 3 | | −6 | 5 | | | |
| 8000-29-1 | 182.20 | Citronella | *Cymbopogon nardus* Rendle | 91 | 1 | | 60 | 4 | | | | | | |
| 8016-63-5 | 182.20 | Clary Sage | *Salvia sclarea* L. | 98 | 2 | | 34 | 4 | | 46 | 4 | 50.03 (0.05); 6 (3) | | |
| 8000-34-8 | 184.1257 | Clovebud | *Eugenia* spp. | 100 | 0 | | 84 | 1 | | | | | | |
| 8008-52-4 | 182.20 | Coriander | *Coriandrum sativum* L. | 89 | 2 | | 30 | 5 | | | | | | |
| 8014-13-9 | 182.20 | Cumin | *Cuminum cyminum* L. | 100 | 0 | | 52 | 5 | | | | | | |
| 8013-86-3 | | Cypress | *Cupressus sempervirens* L. | 92.3 | 0.5 | | 6 | 3 | | | | | | |
| 8000-48-4 | 172.510 | Eucalyptus | *Eucalyptus globulus* | 93 | 1 | | 65 | 3 | | 23 | 1 | | | |

TABLE 1-continued

ESSENTIAL OILS

| CAS# | CFR# | Name | Latin name | 0.01% | SD | repeat 0.01 (SD) | 0.001% | SD | repeat 0.001 (SD) | 0.001% | SD | repeat 0.0001(SD) | 0.0001% | SD |
|---|---|---|---|---|---|---|---|---|---|---|---|---|---|---|
| 8006-84-6 | 182.20 | Fennel | Foeniculum vulgare Mill. var. dulce D.C. Labille | 89 | 3 | | 35 | 1 | | | | | | |
| 8021-29-2 | | Fir needle, Siberian | Abies siberica | 92 | 1 | | 79 | 10 | | 31 | 2 | | | |
| 8016-36-2 | 172.510 | Frankincense (Olibanum oil) | Boswellia spp. | 97 | 1 | | 33 | 1 | | | | | | |
| 8000-78-0 | 184.1317 | Garlic | Allium sativum L. | 36 | 1 | | | | | | | | | |
| 8000-46-2 | 182.20 | Geranium, Rose | Pelargoneum graveolens L'Her | 92 | 6 | | 68 | 3 | | 3.44 | 0.04 | | | |
| 8007-08-7 | 182.20 | Ginger | Zingiber officinale Rosc. | 100 | 0 | 100 (3) | 78 | 2 | | 23 | 2 | | | |
| 8016-20-4 | 182.20 | Grapefruit | Citrus paradisi Macf. | 88 | 1 | | 29 | 4 | | | | | | |
| 8006-83-5 | 182.20 | Hyssop | Hyssopus officinalis L. | 98.2 | 0.1 | | 60 | 2 | | 14 | 4 | | | |
| 8022-96-6 | 182.20 | Jasmine Absolute | Jasminum grandiflorum L. | 95 | 2 | | 48.4 | 0.5 | | | | | | |
| | | Jojoba | | 1 | 1 | | | | | | | | | |
| 8012-91-7 | 182.20 | Juniper Berry | Juniperus communis L. | 96 | 2 | | 15.9 | 0.4 | | | | | | |
| 8000-28-0 | 182.20 | Lavender | Lavandula angustifolia | 97.8 | 0.1 | | 49.5 | 0.6 | | | | | | |
| 8008-56-8 | 182.20 | Lemon | Citrus limon (L) Burm. f. | 62 | 4 | | 20 | 2 | | | | | | |
| 8007-02-1 | 182.20 | Lemongrass | Cymbopogon citratus DC. & Cymbopogon flexuosus | obscured | | | 52 | 3 | | | | | | |
| 8008-26-2 | 182.20 | Lime | Citrus aurantifolia (christman) Swingle | 91 | 1 | | 36 | 3 | | | | | | |
| 8015-01-8 | 182.20 | Marjoram, sweet | Marjorana hortensis Moench (Origanum marjorana L.) | 94 | 1 | | 54 | 3 | | | | | | |
| | | Mugwort | Verbascum spp. | 98 | 1 | | 65 | 3 | | 30 | 3 | | | |
| 9000-45-7 | 172.510 | Mullein Flower | Commiphora spp. | 47 | 5 | | 74 | 3 | | 15 | 3 | 13 (1) | | |
| 8016-38-4 | 172.510 | Myrrh Gum | Citrus aurantium L. | 100 | 0 | | 44 | 4 | | | | | | |
| 8008-45-5 | 182.20 | Neroli, bigarade | Myristica fragrans houtt. | 98 | 2 | | 22.3 | 0.2 | 100 (0) | | | | | |
| | 182.20 | Nutmeg | | 92 | 2 | | | | | | | | | |
| 8030-28-2 | 182.20 | Orange, Bitter | Citrus aurantium L. | 88 | 3 | | 23 | 3 | | | | | | |
| 68606-94-0 | 182.20 | Orange, Sweet | Citrus sinensis (L.) Osbeck | 66 | 5 | | 33 | 3 | | | | | | |
| 8014-09-3 | | Oregano | Lippia spp. | 99.7 | 0.4 | 100 (0) | 75 | 2 | | 30 | 1 | | | |
| 8013-99-8 | 172.510 | Patchouly | Pogostemon spp. | 100 | 0 | 99 (3) | 100 | 0 | | 64 | 4 | | | |
| | 172.510 | Pennyroyal | Mentha Pulegium | 99 | 1 | | 57 | 5 | | | | | | |
| 8006-82-4 | 182.20 | Pepper, Black | Piper nigrum L. | 98 | 2 | | 78.3 | 0.3 | | 6 | 3 | | | |
| 8006-90-4 | 182.20 | Peppermint | Mentha piperita L. | 98 | 1 | 100 (0) | 73 | 3 | | 56 | 4 | 47 (1); 41 (2) | 14 | 2 |
| 8014-17-3 | 172.510 | Petitgrain | Citrus aurantium L. | 97 | 1 | 100 (1) | 14 | 3 | | | | | | |
| 8021-21-2 | 172.510 | Pine Needle | Abies spp. | 93 | 1 | 100 (0) | 57 | 3 | | | | 49 (2); 38 (3) | | |

TABLE 1-continued

ESSENTIAL OILS

| CAS# | CFR# | Name | Latin name | 0.01% | SD | repeat 0.01 (SD) | 0.001% | SD | repeat 0.001 (SD) | 0.0001% | SD | repeat 0.0001(SD) | 0.00001% | SD |
|---|---|---|---|---|---|---|---|---|---|---|---|---|---|---|
| 8007-01-0 | 182.20 | Poke Root | | 9 | 2 | | | | | | | | | |
| 8007-01-0 | 182.20 | Rose Absolute | *Rosa spp.* | 99 | 1 | 100 (0) | 40 | 3 | | | | | | |
| 8007-01-0 | 182.20 | Rosehip Seed | *Rosa spp.* | 60 | 5 | 100 (0) | −5 | 4 | | | | | | |
| 8000-25-7 | 182.20 | Rosemary | *Rosemarinus officinalis* L. | 95.5 | 0.3 | | 56 | 2 | | | | | | |
| 8016-64-6 | 182.20 | Sage, Dalmation | *Salvia officinalis* L. | 98 | 1 | 100 (0) | 36 | 1 | | | | | | |
| 8006-87-9 | 172.510 | Sandalwood Oil, Mysore | *Santalum album* L. | 100 | 0 | | 100 | 0 | | 95 | | 2 | 79 (2); 91.9 (0.4) | 11.9 | 0.5 |
| 8006-80-2 | | Sassafras | *Sassafras albidum* (Nutt.) nees (Safrole free) | 93 | 2 | 98 (1) | 51 | 5 | | | | | | |
| 8008-79-5 | 182.20 | Spearmint | *Mentha spicata* L. | 98 | 2 | | 62 | 6 | | 4 | 2 | | | |
| 8022-22-8 | | Spikenard | | obscured | | obscured | obscured | | | | | | | |
| 8008-80-8 | 172.510 | Spruce (Hemlock) | *Tsuga and Picea spp.* | 95.9 | 0.2 | | 35 | 2 | | | | | | |
| 8008-31-9 | 182.20 | Tangerine | *Citrus reticulata* blanco | 91.3 | 0.1 | 100 (0) | 46 | 3 | | | | | | |
| 68647-73-4 | | Tea Tree | *Melaleuca alternifolia* | 95.8 | 0.2 | 98 (4) | 49 | 4 | | | | | | |
| 8007-20-3 | 172.510 | Thuja (Cedar leaf) | *Thuja occidentalis* | 95 | 1 | 100 (0) | 66 | 4 | | 23 | | 4 | | | |
| 8007-46-3 | 182.20 | Thyme | *Thymus vulargis* L. | 97.3 | 0.5 | 100 (0) | 38 | 4 | | | | | | |
| 84650-63-5 | 182.20 | Vanilla Extract | *Vanilla spp.* | 6 | 2 | | | | | | | | | |
| 8016-96-4 | 172.510 | Vetivert | *Vetiveria zizanioides* Stapf. | obscured | | obscured | obscured | | | | | | | |
| 90045-28-6 | 182.20 | Wintergreen | *Gaultheria procumbens* L. | 87 | 1 | 100 (0) | 9 | 5 | | | | | | |
| | | Witch Hazel (Hamamelia) Extract | | 2 | 6 | | | | | | | | | |
| 8006-81-3 | 182.20 | Ylang Ylang (Cananga) Extract | *Cananga odorata* Hook f. and Thomas | 100 | 0 | | 83 | 1 | | 40 | | 3 | 43 (4); −5 (11) | | |

TABLE 2

OIL INGREDIENTS

| CAS# | CFR# | Name | Other names | 0.01% | SD | repeat 0.01 (SD) | 0.001% | SD | repeat 0.001 (SD) | 0.0001% | SD | repeat 0.0001 (SD) |
|---|---|---|---|---|---|---|---|---|---|---|---|---|
| 3016-19-1 | | Allo Ocimene | 2,6-Dimethyl-2,4,6-octatriene | not tested | | | 22 | 4 | | 6 | 1 | |
| 4180-23-8 | 182.60 | Anethole, trans- | 4-Propenylanisole | 100 | 0 | | 53 | 2 | | | | |
| 103-41-3 | 172.515 | Benzyl Cinnamate | Benzyl 3-phenylpropenoic acid | no tested | | | -45 | 6 | | 7 | 2 | |
| 464-45-9 | 172.515 | Borneol-(1S)-endo-(−) | 1,7,7-Trimethylbicyclo [2.2.1] heptan-2-ol | 100 | 0 | | 80 | 3 | | 20 | 3 | |
| 5794-03-6 | 172.515 | Camphene-(+) | 2,2-Dimethyl-3-methylenebicyclo[2.2.1]heptane | not tested | | | 12.4 | 0.9 | | -49 | 19 | |
| 21368-68-3 | 172.515 | Camphor-(±) | 1,7,7-Trimethylbicyclo [2.2.1] heptan-2-one | 87 | 3 | | 57 | 4 | 53 (3) | | | |
| 404-86-4 | | Capsaicin | trans-8-Methyl-N-vanillyl-6 nonenamide | not tested | | | 68 | 2 | | 27 | 3 | |
| 13466-78-9 | | Carene-3-(Δ) | 2,2,5-Trimethylbicyclo [4.1.0] hept-5-ene | not tested | | | 34 | 4 | | -26 | 5 | |
| 499-75-2 | 172.515 | Carvacrol | 5-isoProply-2-methylphenol | 97 | 1 | | 93 | 1 | | 11 | 1 | |
| 99-48-9 | 172.515 | Carveol-(−) | p-Mentha-6,8-dien-2-ol | not tested | | | 60 | 1 | | 2 | 2 | |
| 6485-40-1 | 182.60 | Carvone-(R)-(−) | p-Mentha-6,8-dien-2-one | 100 | 0 | | 69 | 2 | | 27 | 4 | |
| 2244-16-8 | 172.515 | Carvone-(S)-(+) | p-Mentha-6,8-dien-2-one | not tested | | | 70.5 | 0.1 | | 30 | 2 | |
| 87-44-5 | 182.60 | Caryophyllene, trans-(−) | β-Caryophyllene | not tested | | | 85 | 2 | | 26 | 3 | |
| 14371-10-9 | | Cinnamic Aldehyde, trans- | 3-Phenylpropenaldehyde | 78 | 1 | | 29.0 | 0.6 | | | | |
| 5392-40-5 | 182.60 | Citral | Mixed geranial and neral | 99 | 1 | | 54 | 3 | | 44 | 2 | obscured |
| 2385-77-5 | 172.515 | Citronellal-(R)-(+) | 3,7-Dimethyl-6-octenal | 95 | 4 | | 71 | 2 | | 30 | 1 | 20 (4) |
| 5949-05-3 | 172.515 | Citronellal-(S)-(−) | 3,7-Dimethyl-6-octenal | 100 | 0 | | 62 | 2 | | -1 | 1 | |
| 106-22-9 | 172.515 | Citronellol-(DL)-(β) | 3,7-Dimethyl-6-octen-1-ol | 95 | 2 | | 86 | 1 | | 41 | 1 | 35 (4) |
| 140-67-0 | 172.515 | Estragole | 4-Allylanisole | 100 | 0 | | 69.2 | 0.6 | | 7 | 2 | |
| 103-36-6 | 172.515 | Ethyl Cinnamate, trans- | Ethyl 3-phenylpropenoic acid | not tested | | | -16 | 8 | | -13 | 8 | |
| 121-32-4 | 182.60 | Ethyl Vanillin | 3-Ethoxy-4-hydroxybenzaldehyde | 58 | 1 | | 64 | 3 | | 38 | 1 | |
| 470-82-6 | 172.515 | Eucalyptol | 1,8-Cineole | 88 | 1 | | 66 | 1 | | 9.8 | 0.4 | |
| 97-53-0 | 184.1257 | Eugenol | 4-Allyl-2-methoxyphenol | 100 | 0 | | 82 | 3 | | 49 | 4 | |
| 106-28-5 | 172.515 | Farnesol, trans-, trans- | 3,7,11-Trimethyl-2,6,10-dodecatrien-1-ol | not tested | | | | | | | | |
| 2217-02-9 | 172.515 | Fenchol-(1R)-endo-(+) | 1,3,3-Trimethylbicyclo [2.2.1] heptan-2-ol | 100 | 0 | | 74 | 1 | | 18 | 2 | |
| 7787-20-4 | 172.515 | Fenchone-(1R)-(+) | 1,3,3-Trimethylbicyclo [2.2.1] heptan-2-one | not tested | | | 38 | 5 | | 14 | 3 | |
| 106-24-1 | 182.60 | Geraniol | trans-3,7-Dimethyl-2,6-octadien-1-ol | 76 | 7 | | 66.7 | 0.5 | | 40 | 2 | 25(1); -7 (8) |
| 105-87-3 | 182.60 | Geranyl Acetate | trans-3,7-Dimethyl-2,6-octadien-1-yl acetate | 73 | 8 | | 51.5 | 0.1 | | | | |
| 488-10-8 | 172.515 | Jasmone, cis- | 3-Methyl-2-(2-pentenyl)-2-cyclopenten-1-one | not tested | | | 68 | 1 | | 16.0 | 0.4 | |
| 5989-27-5 | 182.60 | Limonene-(R)-(+) | p-Mentha-1,8-diene | 84 | 3 | | 20 | 4 | | | | |
| 5989-54-8 | 182.60 | Limonene-(S)-(−) | p-Mentha-1,8-diene | 82.3 | 0.4 | | 30 | 5 | | | | |
| 78-70-6 | 182.60 | Linalool-(±) | 3,7-Dimethyl-1,6-octadien-3-ol | 85 | 1 | | 72.0 | 0.1 | | 41 | 2 | -7 (9); -5 (2) |
| 115-95-7 | 182.60 | Linalyl Acetate | 3,7-Dimethyl-1,6-octadien-3-yl acetate | 100 | 0 | | 55.8 | 0.7 | | | | |

TABLE 2-continued

OIL INGREDIENTS

| CAS# | CFR# | Name | Other names | 0.01% | SD | repeat 0.01 (SD) | 0.001% | SD | repeat 0.001 (SD) | 0.0001% | SD | repeat 0.0001 (SD) |
|---|---|---|---|---|---|---|---|---|---|---|---|---|
| 15356-70-4 | 182.20 | Menthol-(±) | p-Menthan-3-ol | 100 | 0 | | 79 | 2 | | 20 | 4 | |
| 14073-97-3 | 172.515 | Menthone-(−) | p-Menthan-3-one | not tested | | | 52 | 3 | | 14 | 3 | |
| 134-20-3 | 182.60 | Methyl Anthranilate | Methyl 2-aminobenzoate | not tested | | | 23 | 1 | | −7 | 6 | |
| 1211-29-6 | | Methyl Jasmonate-(±) | Methyl-3-oxo-2-(2-pentenyl)-cyclopentane acetate | not tested | | | 65 | 2 | | −27 | 5 | |
| 119-36-8 | | Methyl Salicylate | Methyl 2-hydroxybenzoate | 86 | 1 | | 12 | 3 | | 0 | | |
| 123-35-5 | 172.515 | Myrcene-β | 7-Methyl-3-methylene-1,6-octadiene | not tested | | | 13 | 2 | | | 1 | |
| 106-25-2 | 172.515 | Nerol | cis-3,7-dimethyl-2,6-octadien-1-ol | 100 | 0 | | 81.0 | 0.6 | | 54 | 4 | 37 (2); 12 (2) |
| 7785-70-8 | 172.515 | Pinene-(+)-α | 2,6,6-Trimethylbicyclo [3.1.1] hept-2-ene | not tested | | | 23 | 2 | | −9 | 3 | |
| 18172-67-3 | 172.515 | Pinene-(1S)-(−)-β | 6,6-Dimethyl-2-methylenebicyclo[3.1.1]heptane | 88 | 3 | | 60 | 2 | | −10 | 1 | |
| 89-82-7 | 172.515 | Pulegone-(R)-(+) | p-Menth-4(8)-en-3-one | not tested | | | 31 | 4 | | −17 | 5 | |
| 562-74-3 | | Terpinen-4-ol | p-Menth-1-en-4-ol | 100 | 0 | | 80 | 2 | | 3.81 | 0.03 | |
| 99-86-5 | 172.515 | Terpinene-α | p-Mentha-1,3-diene | not tested | | | 28 | 5 | | −6 | 5 | |
| 10482-56-1 | 172.515 | Terpineol-α | p-Menth-1-en-8-ol | 100 | 0 | | 86 | 3 | | 13.4 | 0.2 | |
| 89-83-8 | 172.515 | Thymol | 2-isoPropyl-5-methylphenol | 100 | 0 | | 56 | 2 | | | | |

TABLE 3

REFERENCE COMPOUNDS

| CAS # | CFR # | Name | Other names | % | 0.01% | SD | repeat (SD) |
|---|---|---|---|---|---|---|---|
| 64-17-5 | 184.1293 | Ethanol | Ethyl alcohol | 1 | 44 | 4 | 42 (4); 49 (4); 45 (8) |
| 64-17-5 | 184.1293 | Ethanol | | 0.5 | 33.2 | 0.2 | |
| | | Ketoconazole | | 0.00005 | 100 | 0 | |
| | | Ketoconazole | | 0.00001 | 42 | 3 | |
| | | Ketoconazole | | 0.000005 | 20 | 3 | |
| | | Ketoconazole | | 0.000001 | 8 | 3 | |

Surprisingly, it has also been discovered that individual components of essential oils tested to date (Table 2) are often not as effective in enhancing bioavailability as the essential oils themselves, which are usually complex mixtures of compounds (usually hydrocarbons and oxygenated hydrocarbons). Thus the essential oils appear to be operating as synergistic compositions, perhaps because of the ability of different components of the oils to inhibit different biological pathways associated with bioavailability. While the inventors do not wish to be bound by speculation, it is possible that minor components present in essential oils of all plants may be involved; it is known for example that many essential oil components are terpene derivatives, and there may be identical or structurally similar minor components present in most if not all plant oils. Thus full essential oils represent a preferred embodiment of the invention.

As is apparent, since use of one essential oil that contains numerous components and is a mixture is within the scope of the present invention, use of a mixture of essential oils (and/or components) will also be within the scope of the invention.

Bioavailability Measurements

The increase in drug bioavailability attributable to administration of the essential oil can be determined by measuring total systemic drug concentrations over time after coadministration of a drug and the essential oil and after administration of only the drug. The increase in drug bioavailability is defined as an increase in the Area Under the Curve (AUC). AUC is the integrated measure of systemic drug concentrations over time in units of mass-time/volume. The AUC from time zero (the time of dosing) to time infinity (when no drug remains in the body) following the administration of a drug dose is a measure of the exposure of the patient to the drug. When efficacy of the essential oil is being measured, the amount and form of active drug administered should be the same in both the coadministration of drug and essential oil and the administration of the drug alone. For instance, administration of 10 mg of drug alone may result in total systemic drug delivered over time (as measured by AUC) of 500 μg-hr/ml. In administration (i.e., in the presence of the essential oil) the systemic drug AUC may increase to 700 μg-hr/ml. If significantly increased drug bioavailability in the presence of the essential oil is anticipated, drug doses may need to be reduced for safety.

Systemic drug concentrations are measured using standard in vitro or in vivo drug measurement techniques. "Systemic drug concentration" refers to a drug concentration in a mammal's bodily fluids, such as serum, plasma or blood; the term also includes drug concentrations in tissues bathed by the systemic fluids, including the skin. Systemic drug concentration does not refer to digestive fluids. The increase in total systemic drug concentrations is one way of defining an increase of drug bioavailability due to coadministration of essential oil and drug. For drugs excreted unmetabolized in the urine, an increased amount of unchanged drug in the urine will reflect the increase in systemic concentrations.

Characteristics of Drugs Used With Essential Oils

The word "drug" as used herein is defined as a chemical capable of administration to an organism which modifies or alters the organism's physiology. More preferably the word "drug" as used herein is defined as any substance intended for use in the treatment or prevention of disease. Drug includes synthetic and naturally occurring toxins and bio-affecting substances as well as recognized pharmaceuticals, such as those listed in "The Physicians Desk Reference," 49th edition, 1995, pages 101–338; "Goodman and Gilman's The Pharmacological Basis of Therapeutics" 8th Edition (1990), pages 84–1614 and 1655–1715; and "The United States Pharmacopeia, The National Formulary", USP 23 NF 18 (1995), the compounds and compositions of these references being herein incorporated by reference. The term drug also includes compounds that have the indicated properties that are not yet discovered or available in the U.S. The term drug includes pro-active, activated and metabolized forms of drugs. The present invention can be used with drugs consisting of charged, uncharged, hydrophilic, zwitter-ionic, or hydrophobic species, as well as any combination of these physical characteristics. A hydrophobic drug is defined as a drug which in its non-ionized form is more soluble in lipid or fat than in water. A preferred class of hydrophobic drugs is those drugs more soluble in octanol than in water.

Compounds (or drugs) from a number of classes of compounds can be administered with an essential oil. The compound (drug) can be, for example, but is not limited to, the following classes: acetanilides, anilides, aminoquinolines, benzhydryl compounds, benzodiazepines, benzofurans, cannabinoids, cyclic peptides, dibenzazepines, digitalis gylcosides, ergot alkaloids, flavonoids, imidazoles, quinolines, macrolides, naphthalenes, opiates (or morphinans), oxazines, oxazoles, phenylalkylamines, piperidines, polycyclic aromatic hydrocarbons, pyrrolidines, pyrrolidinones, stilbenes, sulfonylureas, sulfones, triazoles, tropanes, and vinca alkaloids.

Increased Drug Bioavailability by Inhibition of Cytochrome P450

Phase I Biotransformation

Reduction of enterocyte cytochromes P450 participation in drug biotransformation is one objective of the present invention. The major enzymes involved in drug metabolism are present in the endoplasmic reticulum of many types of cells but are at the highest concentration in hepatocytes. Traditionally, enterocyte biotransformation was considered of minor importance in biotransformation compared to the liver. Many compounds inhibit cytochrome P450. These include, but are not limited to, ketoconazole, troleandomycin, gestodene, calcium channel blockers (such as diliazaem, nifedepine, and verapamil), erythromycin, ethynyl estradiol, and prednisolone. The first goal of the invention is to use an essential oil to inhibit drug cytochrome P450 biotransformation in the gut to increase drug bioavailability.

Types Of Cytochromes And Tissue Location

The cytochromes P450 are members of a superfamily of hemoproteins. They represent the terminal oxidases of the mixed function oxidase system. The cytochrome P450 gene superfamily is composed of at least 207 genes that have been named based on their evolutionary relationships. For this nomenclature system, the sequences of all of the cytochrome P450 genes are compared, and those cytochromes P450 that share at least 40% identity are defined as a family (designated by CYP followed by a Roman or Arabic numeral, e.g. CYP3), further divided into subfamilies (designated by a capital letter, e.g. CYP3A), which are comprised of those forms that are at least 55% related by their deduced amino acid sequences. Finally, the gene for each individual form of cytochrome P450 is assigned an Arabic number (e.g. CYP3A4).

Three cytochrome P450 gene families (CYP1, CYP2 and CYP3) appear to be responsible for most drug metabolism. At least 25 cytochromes 450 have been characterized to varying degrees in the human liver. At concentrations of the substrates found under physiologic conditions, enzyme kinetics often favor a single form of cytochrome P450 as the primary catalyst of the metabolism of a particular drug or other enzyme substrate.

The CYP3 gene family encoding cytochromes P450 of type 3 is possibly the most important family in human drug metabolism. At least 5 forms of cytochrome P450 are found in the human 3A subfamily, and these forms are responsible for the metabolism of a large number of structurally diverse drugs. In non-induced individuals 3A may constitute 15% of the P450 enzymes in the liver. In enterocytes, members of the 3A subfamily constitute greater than 70% of the cytochrome-containing enzymes. The first two human 3A subfamily members identified were 3A3 and 3A4. These two cytochromes P450 are so closely related that the majority of studies performed to date have not been able to distinguish their contributions, and thus they are often referred to as 3A3/4. Erythromycin N-demethylation, cyclosporine oxidation, nifedipine oxidation, midazolam hydroxylation, testosterone 6β-hydroxylation, and cortisol 6β-hydroxylation are all in vitro probes of 3A3/4 catalytic activity. The levels of 3A3/4 vary by as much as 60-fold between human liver microsomal samples, with the levels of 3A forms approaching 50% of the total cytochrome P450 present in human liver samples from individuals receiving inducers of 3A3/4. The recently studied CYP3A5 may also play a role as important as 3A3/4.

The liver contains many isoforms of cytochrome P450 and can biotransform a large variety of substances. The enterocytes lining the lumen of the intestine also have significant cytochrome P450 activity, and this activity is dominated by a single family of isozymes, 3A, the most important isoforms in drug metabolism.

Increased Drug Efficacy By Reducing CYP3A Drug Biotransformation

Preferred essential oils of the invention reduce drug biotransformation in the gut by inhibiting CYP3A activity in gut epithelial cells which leads to a total increase in drug bioavailability in the serum. In the presence of essential oils, fewer drug molecules will be metabolized by phase I enzymes in the gut and will not be available for phase II conjugation enzymes. This will lead to increased concentrations of untransformed drug passing from the gut into the blood and onto other tissues in the body.

Although the primary objective of the essential oil is to inhibit CYP3A drug biotransformation in the gut, some biotransformation may be decreased in other tissues as well if the essential oil is absorbed into the blood stream. The decrease in biotransformation by other tissues will also increase drug bioavailability. The advantage of targeting a essential oil to the gut, however, is that it allows the use of lower systemic concentrations of essential oil compared to inhibitors that target CYP3A in the liver. After oral administration of an essential oil, concentrations will be highest at the luminal surface of the gut epithelia, not having been diluted by systemic fluids and the tissues of the body. Luminal concentrations that are greater compared to blood concentrations will permit preferential inhibition of CYP3A in gut instead of the liver. Essential oils that preferentially inhibit gut CYP3A will also be a particularly effective means of increasing drug bioavailability while minimizing the effects of greater concentrations of essential oils in tissues other than the gut.

Coadministration of an essential oil will also reduce variability of oral bioavailability. Reduction of drug biotransformation or increased drug absorption will decrease variability of oral bioavailability to some degree because the increase in bioavailability will begin to approach the theoretical maximum of 100% oral bioavailability. The increase in oral bioavailability will be generally larger in subjects with lower oral bioavailability. The result is a reduction in inter-individual and intra-individual variation. Addition of essential oil will reduce inter-individual and intra-individual variation of systemic concentrations of a drug or compound. In the case of a low therapeutic index drug, this could lead to a safer course of therapy.

A Net Increase in Drug Bioavailability Due to a Decrease in the Activity of CYP3A.

The catalytic activities of CYP3A that are subject to inhibition include, but are not limited to, dealkyase, oxidase, and hydrolase activities. In addition to the different catalytic activities of CYP3A, different forms of CYP3A exist with a range in molecular weight (for example, from 51 kD to 54 kD, as shown in Komori et al., *J. Biochem.* 1988, 104:912–16).

Some essential oils reduce CYP3A drug biotransformation by acting either as an inhibitor of CYP3A activity or as a substrate of CYP3A activity. The essential oil (or a component of the essential oil) acting either as the inhibitor or the substrate of CYP3A can act as a competitive, non-competitive, uncompetitive, mixed or irreversible inhibitor of CYP3A drug biotransformation. Additionally, the essential oil can have properties of being a ligand for P-gp or cytochrome P450 or a ligand for either protein.

Selection of Essential Oils by Reduction of CYP3A Drug Biotransformation

The relative ability of compounds to act as bioenhancers and to increase drug bioavailability can be estimated using in vitro and in vivo drug biotransformation measurements. In vivo measurements of drug bioavailability, such as measuring serum or blood drug concentrations over time, provide the closest measure of total drug systemic availability (bioavailability). In vitro assays of CYP3A metabolism and P-gp-transport, as discussed below, indirectly indicate drug bioavailability because CYP3A drug metabolism and P-gp drug transport affect integrated systemic drug concentrations over time. Generally, the ability of a compound being tested to act as a bioenhancer is demonstrated when the addition of the oil to a drug biotransformation assay decreases CYP3A drug biotransformation. Although even a minimally measured increase is all that is required for an essential oil to be useful, a preferred commercially desirable essential oil acting as a CYP3A modulator generally will increase drug bioavailability by at least 10%, preferably by at least 50%, and more preferably by at least 75% of the difference between bioavailability in the presence of the essential oil and total availability of the ingested dosage in the absence of the essential oil. A sufficient amount of orally administered essential oil will provide integrated systemic drug concentrations over time greater than the integrated systemic drug concentrations over time in the absence of essential oil. The actual amount of essential oil to be included in a pharmaceutical composition will vary with the oil and the active ingredient being protected from CYP3A metabolism. The amount of the essential oil will generally be sufficient to provide a concentration in the gut (and/or volume, depending on the desired effect) of from 0.00001 wt. % to 0.01 wt. %. Examples of individual essential oils and appropriate concentrations for an effective dosage are set forth in Table 1. Such amounts will generally be effective, although optimization of the pharmaceutical composition to provide maximum bioavailability should be carried out using the AUC methods described herein, once the components for a particular pharmaceutical composition have been decided upon.

Essential oils that are particularly good inhibitors of enzymes of the P450 3A class can be identified by a variety of bioassays, several of which are set out below.

In vitro CYP3A Assays and Increased Drug Bioavailability

Cell Assays of CYP3A Function and Increased Drug Bioavailability

Cultured cells of either hepatocytes or enterocytes or freshly prepared cells from either liver or gut can be used to determine the activity of an essential oil as a CYP3A inhibitor. Various methods of gut epithelial cell isolation can be used such as the method of Watkins et al., *J. Clin. Invest.* 1985; 80:1029–36. Cultured cells, as described in Schmiedlin-Ren et al., *Biochem. Pharmacol.* 1993; 46:905–918, can also be used. The production of CYP3A metabolites in cells can be measured using high pressure liquid chromatography (HPLC) methods as described in the following section for microsome assays of CYP3A activity.

Microsome Assays of CYP3A Function and Increased Bioavailability

Microsomes from hepatocytes or enterocytes will be used for assays of CYP3A activity. Microsomes can be prepared from liver using conventional methods as discussed in Kronbach et al., *Clin. Pharmacol. Ther* 1988; 43:630–5. Alternatively, microsomes can be prepared from isolated enterocytes using the method of Watkins et al., *J. Clin. Invest.* 1987; 80:1029–1037. Microsomes from gut epithelial cells can also be prepared using calcium precipitation as described in Bonkovsky et al., *Gastroenterology* 1985; 88:458–467. Microsomes can be incubated with drugs and the metabolites monitored as a function of time. In addition the levels of these enzymes in tissue samples can be measured using radioimmunoassays or western blots. Additionally, the production of metabolites can be monitored using high pressure liquid chromatography systems (HPLC) and identified based on retention times. CYP3A activity can also be assayed by colorimetrically measuring erythromycin demethylase activity as the production of formaldehyde as in Wrighton et al., *Mol. Pharmacol.* 1985; 28:312–321 and Nash, *Biochem. J.* 1953; 55:416–421.

Characteristics of Essential oils that Reduce CYP3A Drug Metabolism

Preferred essential oil(s) will bind CYP3A quickly and inhibit while the drug is passing through the enterocyte. After the essential oils reach the heart and are distributed throughout the body the concentrations of the essential oils will be diluted on future passes through the liver. Concentrations of essential oil used in the gut lumen are preferably selected to be effective on gut CYP3A metabolism but, due to dilution, to be less active in other tissues.

The amount of essential oil used for oral administration can be selected to achieve small intestine luminal concentrations of at least 1/10 of the $K_i$ for CYP3A inhibition of drug metabolism or an amount sufficient to increase systemic drug concentration levels, whichever is less. Alternatively, the amount of an inhibitor of cytochrome P450 3A enzyme that will be used in a formulation can be calculated by various assays that are described in detail below. For example, one such assay measures the conversion of cyclosporine to hydroxylated products in an assay system containing 250 μg rat liver microsomes, 1 μM cyclosporine, and 1 mM NADPH in 1 ml of 0.1M sodium phosphate buffer, pH 7.4. The initial inhibitor amount is selected to provide concentrations in the lumen of the small intestine equal or greater than concentrations that reduce the rate of conversion determined by this assay, preferably a rate reduction of at least 10%. While the actual dose of inhibitor in a clinical formulation might be optimized from this initial dosage depending on the results of a clinical trial, the assay as described is sufficient to establish a utilitarian dosage level.

Increased Drug Bioavailability by Inhibition of P-glycoprotein (P-gp)

Increased Drug Absorption By Decreasing P-gp Drug Transport

Essential oils can further increase bioavailability by increasing net drug absorption through the gut wall into the bloodstream. An essential oil will reduce P-gp active drug transport from the enterocyte back into the gut lumen in order to increase the net transport of drugs across the gut epithelium. Epithelia exist in a number of different tissue types including, but not limited to, the epithelia of the skin, liver, kidneys, adrenals, intestine, and colon. Such epithelia would also be affected by systemic administration of P-gp inhibitors, but the major effects of the essential oils will be limited to the gut because of concentration effects resulting from oral delivery.

Because of the many different compounds present in essential oils as well as the many different classes of active pharmaceutical compounds with which they can be used, the oral dosage of both oil and active ingredient present in the formulation (or elsewise as described below) is best determined empirically, as the dosage will depend on the affinity of the inhibitor for P-gp relative to the drug's affinity for P-gp. There are a number of assays available that allow the desired dosage to be readily determined without requiring clinical trials. While the actual dosage of inhibitor in a clinical formulation might be optimized from this initial dosage depending on results of a clinical trial, the assay as described is sufficient to establish a utilitarian dosage level.

Selection of Essential Oils by Reduction of P-gp Drug Transport/Activity

The relative ability of essential oils to increase drug bioavailability can be estimated using in vitro and in vivo drug transport measurements. Preferred essential oils will cause a net increase in drug diffusion resulting from a decrease in active P-gp drug transport activity. The activity of P-gp can be measured either as ATP-dependent membrane transport of a drug or as drug-dependent ATP hydrolysis. P-gp activity or drug flux can be measured using in vitro or in vivo techniques using, but not limited to, voltage-sensitive electrodes or dyes, chemical-sensitive electrodes or dyes, substrate or product analysis, electron microscopy, or coupled assays. The apparent molecular weight of P-gp used in the assay will vary depending on the species, isoform, amount of glycosylation, and molecular weight assay method. Typically, the molecular weight of the P-gp will be approximately 170 kilodaltons.

The essential oil (or one or more of its components), acting as either the inhibitor or the substrate of P-gp, acts as a competitive, uncompetitive, non-competitive, mixed or irreversible inhibitor of P-gp drug transport. The essential oil, as an inhibitor or substrate of P-gp, can be either a transportable or non-transportable ligand of P-gp. The essential oil (or component) can bind to the P-gp on its lumen accessible surface, cytoplasmic accessible surface or membrane spanning region. The essential oil can be a ligand of P-gp, a ligand of cytochrome P450, or a ligand of both, or any combination of the three types of ligands. For example an essential oil can comprise a ligand of P-gp plus a ligand of cytochrome P450 or a ligand of P-gp plus a ligand that binds to both P-gp and cytochrome P450.

Characteristics of essential oils that reduce P-gp drug transport

When an essential oil is used in sufficient amount, the activity of P-gp will be reduced; in particular P-gp drug transport back into the intestinal lumen will be reduced. Sufficient amounts would include amounts necessary to increase integrated systemic concentrations over time of the drug used in conjunction with the essential oil. The concentration of essential oil required to produce a sufficient amount of essential oil for inhibition of P-gp drug transport varies with the delivery vehicle used for the essential oil and the drug. The luminal concentration of the essential oil should be related to the drug's and essential oil's relative affinities for P-gp and the drug concentration used. As the affinity of drug for P-gp increases, the required concentration of the appropriate essential oil will increase. Most essential oils of commercial application will decrease P-gp drug transport by at least 10%, more preferably by at least 50%, and even more preferably by at least 75%.

In vitro P-gp Assays for Bioavailability

Any bioassay that determines whether a given composition inhibits P-gp transport can be used to identify preferred essential oils. A number of such assays are set out below.

Everted Gut Assays

Everted intestine can be prepared by methods known in the art (Hsing et al. *Gastroenterology* 1992; 102:879–85). In these studies rat small intestines turned "inside out" (i.e. the mucosal (or luminal) surface turned outside and the serosal surface inside) are bathed in a drug containing solution with and without the addition of the essential oil. The serosal surface of the small intestine is bathed in a solution that is periodically monitored or changed for the purpose of drug or essential oil measurement. For instance the everted rat small intestines can be bathed in a physiological saline solution loaded with Rhodamine 123 (Rh123) and the flux of Rh 123 monitored into the serosal solution. The addition of a essential oil in this set-up will increase Rh 123 transport into the serosal solution. An increase in drug or Rh 123 bioavailability will be determined as follows:

$$\frac{X}{Y}(100)$$

where Y is the initial rate of Rh 123 transport, and X is the initial rate of rhodamine transport in the presence of an essential oil. The initial rates will be determined as a linear relationship between time and Rh 123 concentration in the luminal solution. Alternatively, the serosal side of rat small intestines is bathed with the drug or essential oil of interest and the mucosal solution is monitored, as described in Hsing et al. (1992).

Selection of a P-gp Inhibitor Based on Cell Growth Assays

This assay can be used to select particularly preferred essential oils. Cells cultured with cytotoxic agents that are known P-gp transport substrates will be grown as controls in the absence of either drug or essential oil. The appK$_i$ (apparent inhibition constant) for cell growth by drugs will be determined by varying the drug concentration in the culture medium. The appK$_i$ will be expressed as the concentration of drug required to produce 50% inhibition of cell growth. Cells will also be grown in the presence of drug and essential oil. The essential oil will act to shift the appK$_i$ to lower drug concentrations necessary for inhibition of cell growth. Cells with MDR can be used in this assay as described in Hait et al., Biochemical Pharmacology 1993, 45:401–406. The method sections of Hait et al. (1993) are herein incorporated by reference. Preferred essential oils will decrease the appK$_i$ for a drug by at least 2 times, more preferably by at least 3 times, and even more preferably by at least 6 times at a non-toxic dosage.

Rhodamine (Rh 123) Cellular Assay of P-gp Drug Transport and Drug Bioavailability Rh123 can be used in a cellular assay to monitor the bioavailability of drugs. Rh 123 transported by P-gp in this system acts as a drug, where P-gp pumps the Rh 123 out of the cell. Single cells or a population of cells can be monitored for the Rh 123 fluorescence which is indicative of P-gp transport. The cell types used will contain a P-gp transporter from a MDR strain such as those listed in Nielsen and Skovsgaard, *Biochimica et Biophysica Acta* 1993; 1139:169–183 and herein incorporated by reference. Cells are loaded with Rh 123 in the presence of 15 nanograms per ml to 500 nanograms per ml of Rh 123 in a physiologically compatible buffer such as 3-N-morpholinopropanesulfonic acid (MOPS) with the suitable concentrations of sodium, potassium, and calcium chloride and an energy source. The cells are loaded with Rh 123 for 30–60 minutes depending on the temperature (37° or room temperature). The loaded cells are then washed and resuspended in buffer free of Rh 123. The efflux of Rh 123 can be determined using a fluorimeter. In the absence of any essential oil Rh 123 will be pumped out of the cell due to the action of P-gp, leading to a reduced amount of Rh 123 fluorescence from the cell.

Addition of a P-gp substrate or inhibitor either by preincubation after the cells have been washed with Rh 123 free buffer or during the efflux of Rh 123 from the cell will cause retention of Rh 123 within the cell. Retention of Rh 123 in the cell will be caused by the addition of an essential oil. Increased drug bioavailability is defined as the increase in Rh 123 retention within the cell. Compounds that increase Rh 123 retention are bioenhancers.

Rh 123 retention in the absence of an essential oil will be determined by total Rh 123 cell fluorescence minus background Rh 123 cell fluorescence. An increase in drug bioavailability due to the addition of the essential oil will be the percentage increase in Rh 123 fluorescence retention as described by:

$$\frac{X}{Y}(100)$$

where X equals Rh 123 fluorescence in the presence of the essential oil minus the background Rh 123 fluorescence and Y equals the Rh 123 fluorescence in the absence of the essential oil minus the background Rh 123 fluorescence.

The background Rh 123 fluorescence can be measured in a variety of ways including, but not limited to, the residual amount of Rh 123 fluorescence at the end of the experiment, the residual mount of Rh 123 fluorescence remaining based on an extrapolation of first order rate kinetics describing the efflux of Rh 123 from the cell, the residual amount of Rh 123 fluorescence in the presence of a sufficient amount of membrane detergents such as triton or digitonin, or the amount of Rh 123 fluorescence in the presence of a potassium-valinomycin clamp.

The addition of both a second drug and an essential oil to the Rh 123 assay will not necessarily cause an increased amount of Rh 123 retention compared to the presence of either the essential oil alone or the second drug alone. This is because Rh 123 retention can already be very high due to the second drug or essential oil concentration. Extra retention due to the addition of either the second drug or the essential oil can be difficult to measure above the signal for Rh 123 in the presence of the second drug or essential oil alone. However, once it has been determined that the essential oil (or second drug alone) increases Rh 123 fluorescence, i.e. decreases Rh 123 efflux, it can be assumed that the essential oil (or second drug alone) is transported by the P-gp transport system.

Vesicle Assays of P-gp Activity and Drug Bioavailability

A particularly preferred assay uses brush border membranes. Brush border membrane vesicles are prepared from the small intestine by methods known in the art, such as, Hsing, S. et al., *Gastroenterology* 1992; 102:879–885. The vesicles will be assayed for the presence of P-gp by using monoclonal antibodies directed to P-gp either using SDS-PAGE gel electrophoresis and western blotting techniques or using immunochemistry and electromicroscopy. Vesicles containing P-gp will be used for drug transport assays.

Drug transport assays consist of measuring the transport of drugs into the vesicles in an adenosine triphosphate (ATP) dependent fashion. Uptake of the drug in the presence of ATP will be monitored using fluorescence or absorbance techniques, for instance using Rh 123 as the fluorescent drug transported into the interior of the vesicle. Radioactively labeled drugs can also be used to monitor drug transport into the interior of the vesicle using a filter wash system. The addition of ATP will induce the transport of the drug into the vesicle and will increase drug transport compared to passive diffusion of the drug into the vesicle interior. Addition of non-hydrolyzable analogs of ATP such as ATP gamma S or adenosine monophosphate para-nitrophenol (AMP-PNP) will not produce an ATP dependent influx of drug into the vesicle. Thus, the introduction of a non-hydrolyzable nucleotide can be used as a control to monitor whether drug transport has actually occurred due to ATP hydrolysis from the P-gp transport system.

The addition of an essential oil to this assay system, using a fluorescent drug or a radioactive drug and monitoring its uptake, will reduce the uptake of the drug into the interior of the vesicle with the addition of ATP. This reduction in drug transport represents an increase of the bioavailability of the drug. The vesicles transporting drugs in an ATP-dependent fashion are oriented with the cytosolic face of P-gp accessible to the ATP. It is these vesicles that hydrolyze the ATP and transport the drug into the interior of the vesicle. The interior of the vesicle in turn corresponds to the luminal surface or the apical membrane of the brush border cells. Thus, transport into the lumen of the vesicle or interior of the vesicle corresponds to transport into the lumen of the gut. A decrease in the transport into the lumen of the vesicle is the equivalent of increasing net drug absorption and increasing the drug bioavailability.

P-gp ATPase Assays of P-gp Activity and Drug Bioavailability

P-gp molecules can be isolated in vesicles suitable for measuring ATPase activity. P-gp ATPase activity will be measured in the presence of other types of ATPase inhibitors, such as, but not limited to, sodium potassium ATPase inhibitors (ouabain and vanadate), mitochondrial ATPase inhibitors such as oligomycin, and alkaline phosphatase inhibitors. The ATPase assays will also be conducted in the absence of sodium and potassium to eliminate background sodium and potassium ATPase activity. ATPase activity will be measured as ATPase activity dependent on the presence of a drug such as daunomycin. ATPase activity will be measured using ATP or hydrolyzable ATP analogs such para-nitrophenolphosphate. The production of product will be monitored using phosphate assay procedures of those of Yoda, A. and Hokin, L., *Biochem. Biophys. Res. Comm.* 1970, 40:880–886 or by monitoring phosphatase activity as recognized in the literature.

A decrease in P-gp ATPase activity due to the addition of an essential oil is recognized as an increase in drug bioavailability. P-gp molecules located in the brush border membrane vesicles are oriented so the cytosolic portion of the molecule finds and hydrolyzes ATP. It is these P-gp molecules that will give rise to the drug dependent ATPase activity. An essential oil that is able to inhibit the ATPase activity will be able to compete with the drug for the P-gp transport system. Such essential oils will decrease P-gp drug transport due to their increased ability to inhibit P-gp activity.

Another manner of determining the amount of essential oil appropriate for an oral formulation is based on the $K_i$ of the specific inhibitor (for whichever binding is being measured). An appropriate amount of inhibitor is one that is sufficient to produce a concentration of the essential oil in the lumen of the gut of the animal of at least 0.1 times the $K_i$ of the essential oil.

In all of these cases, the goal of selecting a particular concentration is increased bioavailability of the pharmaceutical compound that is being administered. Thus, a desirable goal is to provide integrated systemic concentrations over time of the pharmaceutical compound in the presence of the inhibitor that is greater than the integrated systemic concentrations over time of the pharmaceutical compound in the absence of the inhibitor by at least 10% of the difference between bioavailability in its absence and complete oral bioavailability. Preferred is attaining of "complete bioavailability," which is 100% systemic bioavailability of the administered dosage.

Screening Assay for Superior Essential Oils

In summary, the various techniques described above for screening candidate essential oil compounds for activity levels by assaying for inhibition in the gut of a mammal of activity of a cytochrome P450 enzyme or of transport by P glycoprotein are all generally useful as methods of identifying compounds that are most useful for increasing bioavailability of a drug in a mammal. In all of these assays, the best essential oils are those compounds selected from the candidate compounds being tested that best inhibit either transport or enzymatic destruction (preferably the latter) of a tested drug in the gut of the mammal (either by direct testing in vivo or by a test that predicts such activity). When testing for inhibition of activity of a cytochrome P450 enzyme, assays that detect inhibition of members of a cytochrome P450 3A family (for a particular mammal, particularly human) are preferred. Although in vivo assays are preferred, because of the direct relationship between the measurement and gut activity, other assays, such as assays for inhibition of cytochrome P450 activity in isolated enterocytes or microsomes obtained from enterocytes of the mammal in question or for inhibition of cytochrome P450 in a tissue or membrane from the gut of said mammal, are still useful as screening assays. The same ordering of preferred screening assays (i.e., in vivo being preferred over in vitro) is also preferred for screening of inhibition of P-gp transport. Screening by assaying for both inhibitions is preferred, with inhibition of cytochrome P450 activity generally being more important than that of P-gp-mediated transport.

Coadministration and Delivery of Essential oils

Coadministration of an Essential Oil and a Drug

The present invention will increase the bioavailability of a drug in systemic fluids or tissues by co-administering the essential oil with a drug. "Co-administration" includes concurrent administration (administration of the essential oil and drug at the same time) and time-varied administration (administration of the essential oil at a time different from that of the drug), as long as both the essential oil and the drug are present in the gut lumen and/or membranes during at least partially overlapping times. "Systemic fluids or tissues" refers to blood, plasma, or serum and to other body fluids or tissues in which drug measurements can be obtained.

Delivery Vehicles and Methods

Coadministration can occur with the same delivery vehicle or with different delivery vehicles. The essential oil and the drug can be administered using, as examples, but not limited to, liquid soft/hard gel caps, time release capsules, time release matrices, time release coatings, companion ions, and successive oral administrations. Alternatively, the drug and the essential oil can be separately formulated with different coatings possessing different time constants for release of essential oil and drug.

In addition to simply being mixed with the drug being protected in a pharmaceutical composition the essential oils can also include combinations of compounds of different properties. For example, a first compound can act alone or primarily as a P-gp inhibitor while a second compound acts alone or primarily as a CYP3A inhibitor. Essential oils can also be bound to the drug being protected, either by covalent bonding or by ionic or polar attractions.

Essential oils also increase bioavailability when used with epithelia tissues other than the gut. The discussion above of the invention as used in the gut is appropriate for other types of epithelia. For example, CYP 3A enzymes are known to be present in the skin, and essential oils can be used in transdermal formulations to increase drug bioavailability to systemic fluids and tissues. Such applications are part of the invention, since inhibition of CYP 3A enzymes (and P-glycoprotein) by essential oils in epithelia other than the gut provides the same mechanism of action.

Formulations of Essential oils

The invention is carried out in part by formulating an oral pharmaceutical composition to contain an essential oil. This is accomplished in some embodiments by admixing a pharmaceutical compound, in most cases a pharmaceutical carrier, and an essential oil, the essential oil being present in an amount sufficient to provide integrated systemic concentrations over time of the compound (as measured by AUC's greater than the integrated systemic concentrations over time of the compound in the absence of the composition) when the pharmaceutical composition is administered orally to an animal being treated. A pharmaceutical carrier is generally an inert bulk agent added to make the active ingredients easier to handle and can be solid or liquid in the usual manner as is well understood in the art. Pharmaceutical compositions produced by the process described herein are also part of the present invention.

The present invention can also be used to increase the bioavailability of the active compound of an existing oral pharmaceutical composition. When practiced in this manner, the invention is carried out by reformulating the existing composition to provide a reformulated composition by admixing the active compound with an essential oil, the essential oil being present in an amount sufficient to provide integrated systemic concentrations over time of the compound when administered in the reformulated composition greater than the integrated systemic concentrations over time of the compound when administered in the existing pharmaceutical composition. All of the criteria described for new formulations also apply to reformulation of old compositions. In preferred aspects of reformulations, the reformulated composition comprises all components present in the existing pharmaceutical composition plus the essential oil, thus simplifying practice of the invention, although it is also possible to eliminate existing components of formulations because of the increase in bioavailability. Thus, the invention also covers reformulated compositions that contain less than all components present in the existing pharmaceutical composition plus the essential oil. However, this invention does not cover already existing compositions that contain a component which increases bioavailability by mechanisms described in this specification (even without knowledge of the mechanisms), should such compositions exist.

Traditional formulations can be used with essential oils. Optimal essential oil doses can be determined by varying the amount and timing of essential oil administration and monitoring bioavailability. Once the optimal essential oil dose is established for a drug, the formulation (essential oil, drug, and other formulation components, if any) is tested clinically to verify the increased bioavailability. In the case of time- or sustained-release formulations, it will be preferred to establish the optimal essential oil dose using such formulations from the start of the bioavailability experiments.

Many of the essential oils have been used in flavorings under many different circumstances, and it is possible that they have been used as flavorings in pharmaceutical compositions. However, flavorings are used in small quantities, and such materials are not likely to approach even the outer limits of the present invention as defined by the specification and claims. In particular, preferred formulations of the invention contain at least 1% by weight essential oil relative to the total weight of the formulation (including the capsule, if present), more preferably at least 2%, even more preferably at least 5%. In most cases essential oils used as flavorings are used at less than 0.1% of the materials they are being used to flavor. In considering these percentages, it should be recalled that these are percentages of the formulation in which the active ingredient is being presented, not percentages by weight or volume as concentrations in the medium in which the pharmaceutical composition will become dissolved or suspended after ingestion of the formulation (the latter being the % values shown at other locations in this specification, such as in Table 1).

Furthermore, since many essential oils as well as many of the essential oil components are liquids, such materials will often be used in capsules (either hard or soft standard pharmaceutical gel capsules, for example). Flavorings have generally not been used with capsules, since the capsule protects the user from any disagreeable flavor or odor resulting from the active pharmaceutical compound or other components of the formulation that are present. Presentation of an essential oil in a pharmaceutical capsule is thus a preferred embodiment of the invention.

Table 4 sets forth a number of exemplary formulations to illustrate the invention. Two essential oils are shown in the formulations, peppermint oil and carrot seed oil, that have similar rates of inhibition (56% for peppermint oil at a concentration of 0.0001% in the assay medium, and 52% for carrot seed oil at the same concentration). A simple calculation based on the % inhibition values of Tables 1 or 2 or on assay data for compounds not listed in the Tables would provide the amount of other inhibitors necessary to achieve the same effect. The other ingredients shown in the formulations are standard ingredients used in pharmaceutical compositions and can be readily substituted by other antioxidants, surface active agents (SSA), etc. In Table 4, "alpha tocoph" is alpha-tocopherol, "BHA" is butylated hydroxy anisole, "PVP" is polyvinylpyrrolidone, "Klucel" is hydroxypropyl cellulose, a "bile salt" is cholic acid and/or its sodium salt or a similar salt of a bile acid such as deoxycholic acid or glycholic acid, "Tween" is a commercially available surfactant of the Tween class such as Tween 21 or 81, and "fatty acid" is a naturally occurring fatty acid or a simple (e.g., ethyl) ester thereof.

suspension in corn oil. On day 5 rats were sacrificed by decapitation, and the livers were excised and perfused with 0.15M potassium chloride solution until free of blood. Perfused livers were maintained on ice during all subsequent manipulations.

Preparation of rat liver microsomes

Perfused livers were manually homogenized with 0.1M phosphate buffer (pH 7.4) then the homogenates were centrifuged at 9,000 g for 20 minutes. Supernatants from the initial centrifugation were transferred to ultracentrifuge tubes and centrifuged at 100,000 g for 60 minutes. Supernatants from the ultracentrifugation were discarded, and the residual microsomal pellet was suspended in 0.15M potassium chloride (approximately 25 ml) and centrifuged at 100,000 g for 30 minutes. The supernatant was again discarded, and the microsomal pellet was suspended in 0.1M phosphate buffer. Then the protein and cytochrome P450 concentrations of the microsomal suspensions were determined using the methods of Bradford (M. Bradford Anal. Biochem. 72:248 [1976]) and Omura and Sato (T. Omura and R. Sato J. Biol. Chem. 239:2370 [1964]) respectively. Microsomal suspensions were stored at −80° C. prior to use in metabolic incubations.

Microsomal incubations

Rat liver microsomes (250 µg/ml), diethylenetetraminepentaacetic acid (1 mM), cyclosporine (1 µM; 0.0001%), and either the candidate metabolic inhibitor (0.01%, 0.001%, 0.0001%) or the solvent in which it was dissolved (ethanol or buffer) in 0.1 M phosphate buffer pH 7.4 (total volume of 990 µl were preincubated for 5 minutes at 37° C. in borosilicate glass culture tubes (16 mm×100 mm) using a

TABLE 4

FORMULATION EXAMPLES-CYCLOSPORINE

| (all amounts are mg per capsule) | A | B | C | D | E | F | G | H |
|---|---|---|---|---|---|---|---|---|
| CYCLSPORINE | 100 | 100 | 100 | 100 | 100 | 100 | 100 | 100 |
| ANTI-OXIDANT | | | | | | | | |
| ALPHA TOCOPH | 180 | 180 | 180 | 180 | | | | |
| BHA | | | 0.7 | 0.7 | 0.7 | 0.7 | 0.7 | 0.7 |
| INHIBITOR | | | | | | | | |
| PEPPERMINT OIL | 100 | 100 | 100 | 100 | | | | |
| CARROT SEED OIL | | | 100 | 100 | 200 | 200 | 200 | 200 |
| ANTINUCLEATING AGENT | | | | | | | | |
| PVP | 175 | 175 | 87.5 | 87.5 | 87.5 | | | |
| KLUCEL | | | 87.5 | 87.5 | 87.5 | 175 | 175 | 175 |
| SAA | | | | | | | | |
| BILE SALT | 3.5 | | 3.5 | 1.75 | 1.75 | 1.75 | | |
| TWEEN | | 3.5 | | 1.75 | 1.75 | 1.75 | 3.5 | 3.5 |
| SOLVENT | | | | | | | | |
| ETHYL ALCOHOL | 141.5 | 141.5 | | 40.8 | | 220.8 | | 220.8 |
| FATTY ACID | | | 40.8 | | 220.8 | | 220.8 | |
| TOTAL WT. | 700 | 700 | 700 | 700 | 700 | 700 | 700 | 700 |

The invention now being generally described, the same will be better understood by reference to the following detailed example, which is offered for illustration only and is not to be considered limiting of the invention unless otherwise specified.

EXAMPLE

Inhibition of Drug Degradation by Essential Oils

Induction of rat cytochrome P450 3A with dexamethasone

Ten male Sprague-Dawley rats (250–300 g; Bantin Kingman) received dexamethasone (100 mg/kg) each day for 4 days by intraperitoneal injection of a dexamethasone reciprocal shaking water bath with a constant shaking rate of 100 rpm. Metabolic reactions were started by addition of reduced nicotinamide adenine dinucleotide phosphate (NADPH; 1 mM) to give a total reaction volume of 1 ml. Reactions were conducted in triplicate and were compared to controls without NADPH. Incubations were allowed to proceed for 25 minutes, and the metabolic reactions were stopped by addition of 50:50 acetonitrile:water saturated with zinc sulfate (2 ml) and 100 µl of rotenone internal standard solution (10 µg/ml in reagent alcohol). Samples were vortex mixed for 10 seconds, and then centrifuged for 10 minutes at 5,500 rpm. Supernatants were decanted to new culture tubes, hexane (2 ml) was added, and the mixtures were vortex mixed for 60 seconds. Hexane-washed samples were centrifuged for 5 minutes at 5,500 rpm, and then the upper hexane layer was removed by aspiration through a borosilicate glass Pasteur pipette. The remaining solution was subjected to solid-phase extraction.

Solid-phase extraction

Bond-Elut® LRC C-18 solid-phase extraction columns were fitted to a Vac Elut SPS 24 vacuum manifold (both from Varian Sample Preparation Products, Harbor City, Calif., U.S.A.), and then washed with 2 ml reagent alcohol followed by 2×2 ml distilled water. Hexane-washed supernatants above were drawn onto the washed Bond-Elut® columns by high vacuum, and then the columns were washed with 2×1 ml water and the samples eluted with 1 ml acetonitrile. Acetonitrile solutions were evaporated to dryness under nitrogen, and then dry samples were stoppered and stored frozen until analysis by reverse-phase high pressure liquid chromatography.

Analysis of cyclosporine and metabolites.

Reverse-phase high pressure liquid chromatographic analysis of cyclosporine and metabolites from microsomal incubation mixtures utilized a Beckman model 126 binary solvent module, a Beckman model 168 diode-array ultraviolet absorbance detector, and a Beckman model 507 autosampler with a Rheodyne model 7010 sample injection valve (100 µl sample loop). Data collection and analysis utilized Beckman System Gold™ Personal™ Chromatography Software loaded onto an IBM model 350 466DX2 computer.

Extracted and dried samples from incubation experiments were reconstituted in 65:35 acetonitrile:water (500 µl), and then 100 µl were injected onto a Beckman Ultrasphere® RP-18 analytical column (5 µm; 4.6 mm×250 mm) maintained at 70° C. with an Alltech Adsorbosphere® Direct-Connect™ guard-cartridge system in line with, but not directly attached to, the column. Cyclosporine and metabolites were separated using an acetonitrile-water (pH 3) solvent gradient (65% acetonitrile×4 minutes followed by a 1% per minute increase to 75% acetonitrile which was maintained for 6 minutes) and a solvent flow rate of 1 ml/minute. Cyclosporine and metabolite(s) were detected by ultraviolet absorbance at 214 nm. Rotenone internal standard eluted at 5.6±0.4 minutes, the combined AM1 and AM9 (cyclosporine hydroxylated metabolites) peak eluted at 8.3±0.4 minutes, and cyclosporine eluted at 16.1±0.5 minutes.

Data analysis.

Peak areas for cyclosporine, the combined AM1 and AM9 cyclosporine hydroxylated metabolites peak (AM1&AM9), and the rotenone internal standard were determined from the high pressure liquid chromatography data by integration using Beckman System Gold™ Personal™ Chromatography Software. Cyclosporine metabolism was measured as the peak area ratio of the combined AM1&AM9 peak to the parent cyclosporine, and then the percentage inhibition of cyclosporine metabolism by the candidate inhibitor was determined using the following formula:

Percentage metabolism=100×(1-inhibitor/vehicle)

where "inhibitor"=AM1&AM9/CyA peak area ratio from samples treated with inhibitor and "vehicle"=AM1&AM9/CyA ratio from samples treated with the vehicle (either ethanol or buffer) in which the inhibitor was dissolved for addition to the incubation mixture. Each incubation was conducted in triplicate, and inhibition data are reported as the mean±standard deviation (SD).

Results of Inhibition Assays

The results of these assays are set out in Tables 1-3 above, in which Table 1 shows assay results using essential oils at the stated concentrations, while Tables 2 and 3 show the results of assays using individual components of essential oils as well as the comparison values obtained using the solvents in which the essential oils were dissolved (i.e., negative controls) or ketoconazole, a previously known inhibitor. Essential oils and essential oil components are identified by Chemical Abstracts numbers (CAS#) and by GRAS identifiers as set out in title 21 of the Code of Federal Regulations (CFR#), as well as by common and scientific names. The concentration of oil or other component used in the assay is shown in wt. % in the heading of the appropriate columns, with the % inhibition being shown for the various bioenhancers (a negative value indicates that the component being tested actually reduces bioavailability). In some cases individual assays were repeated and the results are shown. "Obscured," which appears in some columns, means that metabolite peaks were not readily measureable because of the presence of unknown interfering substances in the essential oils.

All publications and patent applications mentioned in this specification are herein incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the appended claims.

We claim:

1. A method for increasing bioavailability of an orally administered hydrophobic pharmaceutical compound, which comprises:

orally administering said pharmaceutical compound to a mammal in need of treatment with said pharmaceutical compound concurrently with an essential oil or a component of an essential oil in an amount of said essential oil or essential oil component sufficient to provide bioavailability of said pharmaceutical compound in the presence of said essential oil or essential oil component greater than bioavailability of said pharmaceutical compound in the absence of said essential oil or essential oil component, and sufficient to provide a concentration of said essential oil or essential oil component in the gut of said mammal equal to or greater than a concentration of said essential oil or essential oil component that reduces conversion of cyclosporine to hydxoxylated products by 10%, compared to controls, in an assay system containing 250 µg rat liver microsomes, 1 µM cyclosporine, and 1 mM reduced nicotinamide adenine dinucleotide phoshate (NADPH) in 1 ml of 0.1M sodium phosphate buffer, pH 7.4.

2. A method for increasing bioavailability of an orally administered hydrophobic pharmaceutical compound, which comprises:

orally administering said pharmaceutical compound to a mammal in need of treatment with said pharmaceutical compound concurrently with an essential oil or a component of an essential oil in an amount of said essential oil or essential oil component sufficient to provide bioavailability of said pharmaceutical compound in the presence of said essential oil or essential oil component greater than bioavailability of said pharmaceutical compound in the absence of said essential oil or essential oil component, and sufficient to provide a concentration of said essential oil or essential oil component in the lumen of the gut of said mammal of at least 0.1 times a $K_i$ or apparent $K_i$ of the essential oil or essential oil component as measured by an assay that measures reduced conversion of cyclosporine to hydroxylated product in an assay system containing 250 μg rat liver microsomes, 1 μM cyclosporine, anal 1 mM reduced nicotinamide adenine dinucleotide phosphate (NADPH) in 1 ml of 0.1M sodium phosphate buffer, pH 7.4.

3. A method of formulating an oral pharmaceutical composition, which comprises:

admixing a pharmaceutical compound, a pharmaceutical carrier, and an essential oil or essential oil component, said essential oil or essential oil component being present in an amount sufficient to provide bioavailability of said pharmaceutical compound in the presence of said essential oil or essential oil component greater than the bioavailability of said pharmaceutical compound in the absence of said essential or oil essential oil component when said pharmaceutical composition is administered orally to a mammal, wherein said essential oil or essential oil component is present in an amount sufficient to provide a concentration of said essential oil or essential oil component in the lumen of the gut of said mammal equal to or greater than a concentration of said essential oil or essential oil component that reduces conversion of cyclosporine to hydroxylated products by 10% in an assay system containing 250 μg rat liver microsomes, 1 μM cyclosporine, and 1 mM NADPH in 1 ml of 0. 1M sodium phosphate buffer, pH 7.4.

4. A method of formulating an oral pharmaceutical composition, which comprise:

admixing a pharmaceutical compound, a pharmaceutical, carrier, and an essential oil or essential oil component, said essential oil or essential oil component being present in an amount sufficient to provide bioavailability of said pharmaceutical compound in the presence of said essential oil or essential oil component greater than the bioavailability of said pharmaceutical compound in the absence of said essential oil or essential oil component when said pharmaceutical composition is administered orally to a mammal, wherein said amount is sufficient to provide a concentration of said essential oil or essential oil component in the lumen of the gut of said mammal of at least 0.1 times said $K_i$ or apparent $K_i$ of said essential oil or essential oil component.

5. The method of claim 3, wherein said essential oil or essential oil component is present as a counter ion of said pharmaceutical compound.

6. The method of claim 3, wherein said essential oil or essential oil component is covalently bound to said pharmaceutical compound.

7. The method of claim 4, wherein said essential oil or essential oil component is present as a counter ion of said pharmaceutical compound.

8. The method of claim 4, wherein said essential oil or essential oil component is covalently bound to said pharmaceutical compound.

9. The method of claim 1, wherein said essential oil or essential oil component comprises 2,6-dimethyl-2,4,6-octatriene; 4-propenylanisole; benzyl-3-phenylpropenoic acid; 1,7,7-trimethylbicyclo[2.2.1]heptan-2-ol;2,2-dimethyl-3-methylenebicyclo[2.2.1]heptane; 1,7,7-trimethylbicyclo[2.2.1]heptane; trans-8-methyl-n-vanillyl-6-nonenamide; 2,2,5-trimethylbicyclo[4.1.0]hept-5-ene; 5-isopropyl-2-methylphenol; p-mentha-6,8-dien-2-ol; p-mentha-6,8-dien-2-one; β-caryophyllene; 3-phenylpropenaldehyde; mixed geranial and neral; 3,7-dimethyl-6-octenal; 3,7-dimethyl-6-octen-1-ol; 4-allylanisole; ethyl 3-phenylpropenoic acid; 3-ethoxy-4-hydroxybenzaldehyde; 1,8-cineole; 4-allyl-2-methoxyphenol; 3,7,11-trimethyl-2,6,10-dodecatrien-1-ol; 1,3,3-trimethylbicyclo[2.2.1]heptan-2-ol; 1,3,3-trimethylbicyclo[2.2.1]heptan-2-one; trans-3,7-dimethyl-2,6-octadien-1-ol; trans-3,7-dimethyl-2,6-octadien-1-yl acetate; 3-methyl-2-(2-pentenyl)-2-cyclopentene-1-one; p-mentha-1,8-diene; 3,7-dimethyl-1,6-octadien-3-ol; 3,7-dimethyl-1,6-octadien-3-yl acetate; p-menthan-3-ol; p-menthan-3-one; methyl 2-aminobenzoate; methyl-3-oxo-2-(2-pentenyl)cyclopentane acetate; methyl 2-hydroxybenzoate; 7-methyl-3-methylene-1,6-octadiene; cis-3,7-dimethyl-2,6-octadien-1-ol; 2,6,6-trimethylbicyclo[3.1.1]hept-2-ene; 6,6-dimethyl-2-methylenebicyclo[3.1.1]heptane; p-menth-4(8)-en-3-one; p-menth-1-en-4-ol; p-mentha-1,3-diene; p-menth-1-en-8-ol; or 2-isopropyl-5-methylphenol.

10. The method of claim 2, wherein said essential oil or essential oil component comprises 2,6-dimethyl-2,4,6-octatriene; 4-propenylanisole; benzyl-3-phenylpropenoic acid; 1,7,7-trimethylbicyclo[2.2.1]heptan-2-ol;2,2-dimethyl-3-methylenebicyclo[2.2.1]heptane; 1,7,7-trimethylbicyclo[2.2.1]heptane; trans-8-methyl-n-vanillyl-6-nonenamide; 2,2,5-trimethylbicyclo[4.1.0]hept-5-ene; 5-isopropyl-2-methylphenol; p-mentha-6,8-dien-2-ol; p-mentha-6,8-dien-2-one; β-caryophyllene; 3-phenylpropenaldehyde; mixed geranial and neral; 3,7-dimethyl-6-octenal; 3,7-dimethyl-6-octen-1-ol; 4-allylanisole; ethyl 3-phenylpropenoic acid; 3-ethoxy-4-hydroxybenzaldehyde; 1,8-cineole; 4-allyl-2-methoxyphenol; 3,7,11-trimethyl-2,6,10-dodecatrien-1-ol; 1,3,3-trimethylbicyclo[2.2.1]heptan-2-ol; 1,3,3-trimethylbicyclo[2.2.1]heptan-2-one; trans-3,7-dimethyl-2,6-octadien-1-ol; trans-3,7-dimethyl-2,6-octadien-1-yl acetate; 3-methyl-2-(2-pentenyl)-2-cyclopenten-1-one; p-mentha-1,8-diene; 3,7-dimethyl-1,6-octadien-3-ol; 3,7-dimethyl-1,6-octadien-3-yl acetate; p-menthan-3-ol; p-menthan-3-one; methyl 2-aminobenzoate; methyl-3-oxo-2-(2-pentenyl)cyclopentane acetate; methyl 2-hydroxybenzoate; 7-methyl-3-methylene-1,6-octadiene; cis-3,7-dimethyl-2,6-octadien-1-ol; 2,6,6-trimethylbicyclo[3.1.1]hept-2-ene; 6,6-dimethyl-2-methylenebicyclo[3.1.1]heptane; p-menth-4(8)-en-3-one; p-menth-1-en-4-ol; p-mentha-1,3-diene; p-menth-1-en-8-ol; or 2-isopropyl-5-methylphenol.

* * * * *